United States Patent
Ishikawa et al.

(10) Patent No.: US 9,629,582 B2
(45) Date of Patent: Apr. 25, 2017

(54) APNEA EPISODE DETERMINATION DEVICE AND APNEA EPISODE DETERMINATION METHOD

(71) Applicant: FUJITSU LIMITED, Kawasaki (JP)

(72) Inventors: Chisato Ishikawa, Kawasaki (JP); Taro Togawa, Kawasaki (JP); Takeshi Otani, Kawasaki (JP); Masanao Suzuki, Yokohama (JP); Asako Nishida, Setagaya (JP)

(73) Assignee: FUJITSU LIMITED, Kawasaki (JP)

( * ) Notice: Subject to any disclaimer, the term of this patent is extended or adjusted under 35 U.S.C. 154(b) by 698 days.

(21) Appl. No.: 13/692,463

(22) Filed: Dec. 3, 2012

(65) Prior Publication Data
US 2013/0261485 A1    Oct. 3, 2013

(30) Foreign Application Priority Data

Mar. 27, 2012 (JP) ................................ 2012-071766

(51) Int. Cl.
  *A61B 5/08*    (2006.01)
  *A61B 5/00*    (2006.01)
  *A61B 7/00*    (2006.01)

(52) U.S. Cl.
  CPC ............ *A61B 5/4818* (2013.01); *A61B 7/003* (2013.01); *A61B 5/7257* (2013.01)

(58) Field of Classification Search
  CPC ..... A61B 7/003; A61B 5/7282; A61B 5/0826; A61B 5/4818; A61B 5/4806–5/4821; A61B 7/04–7/045
  USPC ....................................................... 600/529
  See application file for complete search history.

(56) References Cited

U.S. PATENT DOCUMENTS

| | | | |
|---|---|---|---|
| 6,168,568 B1 * | 1/2001 | Gavriely | A61B 5/087 600/529 |
| 6,261,238 B1 * | 7/2001 | Gavriely | 600/532 |
| 6,375,621 B1 * | 4/2002 | Sullivan | A61B 5/113 600/484 |
| 7,559,903 B2 * | 7/2009 | Moussavi et al. | 600/538 |
| 2004/0010202 A1 * | 1/2004 | Nakatani et al. | 600/529 |

(Continued)

FOREIGN PATENT DOCUMENTS

| | | |
|---|---|---|
| EP | 2457504 A1 * | 5/2012 |
| JP | 2001-23928 | 2/2001 |

(Continued)

OTHER PUBLICATIONS

Extended European Search Report dated Jul. 16, 2013 in European Patent Application No. 12195591.8-1660.

*Primary Examiner* — Christian Jang
(74) *Attorney, Agent, or Firm* — Staas & Halsey LLP

(57) ABSTRACT

An apnea episode determination device includes, a processor; and a memory which stores a plurality of instructions, which when executed by the processor, cause the processor to execute, detecting a breathing segment and a midway segment from a sound signal during sleep, the breathing segment being considered to include a breathing sound, the midway segment existing in between the breathing segments; calculating an acoustic feature based on a background noise component and a signal component excluding the background noise component, which are included in the midway segment; and determining that the midway segment is an apnea episode when the acoustic feature meets a preset condition.

13 Claims, 20 Drawing Sheets

(56) References Cited

U.S. PATENT DOCUMENTS

| | | | |
|---|---|---|---|
| 2005/0065447 A1* | 3/2005 | Lee et al. | 600/529 |
| 2007/0093724 A1 | 4/2007 | Nakano | |
| 2007/0118054 A1* | 5/2007 | Pinhas et al. | 600/587 |
| 2011/0054339 A1* | 3/2011 | Gass et al. | 600/529 |
| 2012/0071741 A1* | 3/2012 | Moussavi et al. | 600/340 |
| 2012/0190996 A1 | 7/2012 | Tanaka et al. | |
| 2013/0331722 A1* | 12/2013 | Rodriguez-Villegas et al. | 600/529 |
| 2014/0188006 A1* | 7/2014 | Alshaer et al. | 600/586 |

FOREIGN PATENT DOCUMENTS

| | | |
|---|---|---|
| WO | WO 2011/010384 | 1/2011 |
| WO | WO 2011010384 A1 * | 1/2011 |

* cited by examiner

APNEA EPISODE DETERMINATION DEVICE AND APNEA EPISODE DETERMINATION METHOD

CROSS-REFERENCE TO RELATED APPLICATION(S)

This application is based upon and claims the benefit of priority of the prior Japanese Patent Application No. 2012-071766, filed on Mar. 27, 2012, the entire contents of which are incorporated herein by reference.

FIELD

The embodiments discussed herein are related to apnea episode determination devices, apnea episode determination methods, and computer-readable recording media on which apnea episode determination programs are recorded, for screening sleep apnea syndrome.

BACKGROUND

Sleep apnea syndrome is defined as a condition in which an apnea episode where cessation of breathing for ten seconds or longer occurs 30 times or more during seven hours of sleep or five times or more per hour of sleep. Sleep apnea syndrome causes symptoms such as uncontrollable daytime sleepiness, depression, impaired concentration, snoring, etc. Furthermore, since a patient with sleep apnea syndrome is asleep when apnea episodes occur, in many cases, finding of sleep apnea syndrome is delayed when the patient does not have any other person to live with, such as family members, etc.

In order to receive a complete examination of sleep apnea syndrome, hospitalization in a hospital having a rooms equipped with data monitoring devices for the examination and analysis of data thus monitored by a medical specialist are recommended. In other words, a patient not only has a burden of costs and time, but also has a physical burden since the patient is often asked to wear sensors on his/her body.

In view of the above, it is desirable to provide a method that allows an individual person to detect the presence or absence of an apnea episode during sleep simply at home, etc.

Simple methods for detecting an apnea episode during sleep may include, for example, a method disclosed in Japanese Laid-open Patent Publication No. 2001-029328 that records a sound during sleep and determines an occurrence of apnea episode when a state where the sound is equal to or less than a predetermined threshold continues for a certain period of time or longer. Furthermore, for example, International Publication Pamphlet No. WO 2011/010384 discloses a method that records a sound during sleep and detects an apnea episode based on a sudden sound uttered immediately after the apnea episode (for example, short breathing, groan).

SUMMARY

In accordance with an aspect of the embodiments, an apnea episode determination device includes, a processor; and a memory which stores a plurality of instructions, which when executed by the processor, cause the processor to execute, detecting a breathing segment and a midway segment from a sound signal during sleep, the breathing segment being considered to include a breathing sound, the midway segment existing in between the breathing segments; calculating an acoustic feature based on a background noise component and a signal component excluding the background noise component, which are included in the midway segment; and determining that the midway segment is an apnea episode when the acoustic feature meets a preset condition.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

These and/or other aspects and advantages will become apparent and more readily appreciated from the following description of the embodiments, taken in conjunction with the accompanying drawing of which.

DESCRIPTION OF EMBODIMENTS

Hereinafter, embodiments of the present disclosed technology are described with reference to the attached drawings. The following configurations of embodiments are provided as examples, and the present disclosed technology is not limited thereto.

For example, when a volume of breathing sound to be recorded is small due to a posture of a subject such as a posture facing away from a microphone or the like, it may be difficult to determine that a midway segment positioned in between breathings includes no breathing sound and therefore an apnea episode by using the sound volume as a basis of determination. Thus, in the first embodiment, an apnea episode is detected by use of an acoustic feature based on a signal component.

Sound signals often include background noises. For example, a sleep sound recorded in a typical house's bedroom may often include, in addition to a breathing sound from a subject, a background noise of the room, a noise inside the house, and an outside noise (for example, automobile noises, construction noises, etc.).

Figure 1:
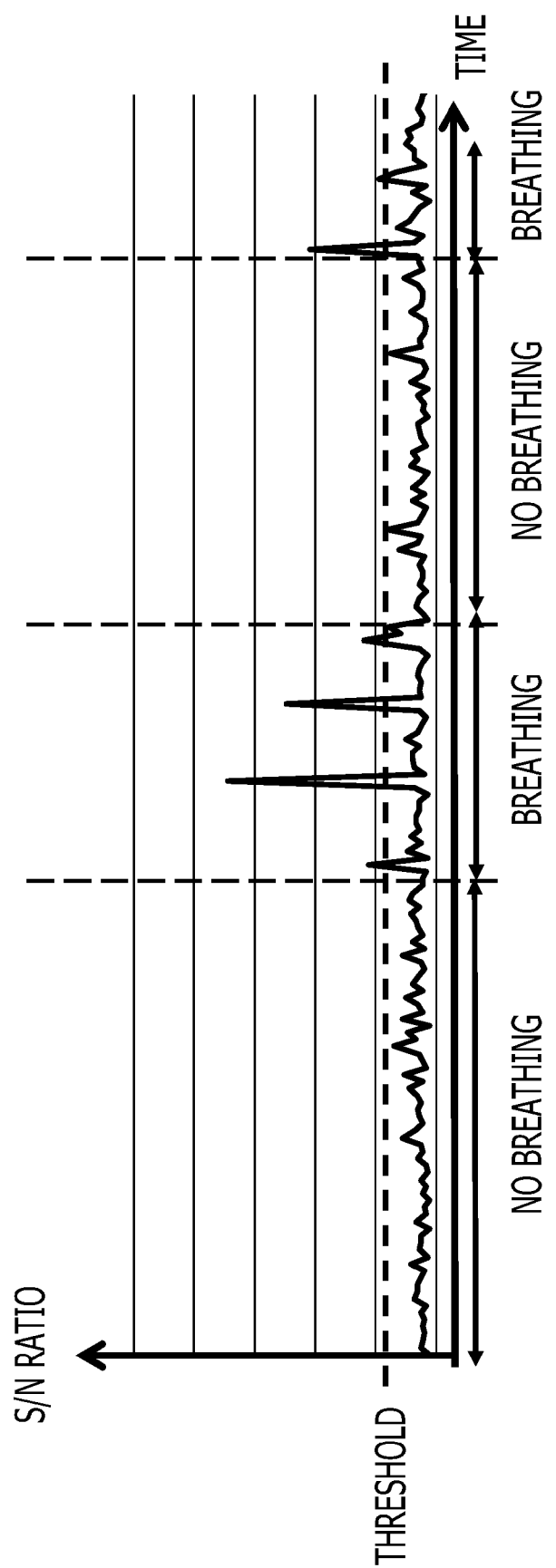
FIG. 1 is a diagram illustrating an example of signal-to-noise ratio of sound data for cases where a breathing sound is included and cases where the breathing sound is not included.

FIG. 1 is a diagram illustrating an example of signal-to-noise ratio of sound data for segments including the breathing sound and segments including no breathing sound. In FIG. 1, the segment including the breathing sound is denoted as "BREATHING", and the segment including no breathing sound is denoted as "NO BREATHING". Assuming that the same level of background noise is included in successive segments, which are the segment including the breathing sound and the segment including no breathing sound, the segment including the breathing sound is less affected by the noise when comparing the segment including the breathing sound with the segment including no breathing sound. Accordingly, as illustrated in FIG. 1, the signal-to-noise ratio in the segment including the breathing sound becomes higher than a preset threshold. On the other hand, the segment including no breathing sound is more affected by the noise, for no breathing sound is included therein. Thus, the signal-to-noise ratio in the segment including no breathing sound becomes lower than the preset threshold. As described above and as illustrated in FIG. 1, the use of the signal-to-noise ratio of the sound data enables to clearly distinguish the segment including the breathing sound from the segment including no breathing sound, irrespective of the sound volume.

Thus, in the first embodiment, an apnea episode determination device detects an apnea episode by using the signal-to-noise ratio as the acoustic feature based on the background noise component and the signal component excluding the background noise component. More specifically, the apnea episode determination device calculates the signal-to-noise ratio in a midway segment between breathings from sound data collected by a microphone or the like during sleep of a subject, and determines that the midway segment is an apnea episode.

<Configuration of Sleep Apnea Episode Determination Device>

Figure 2:
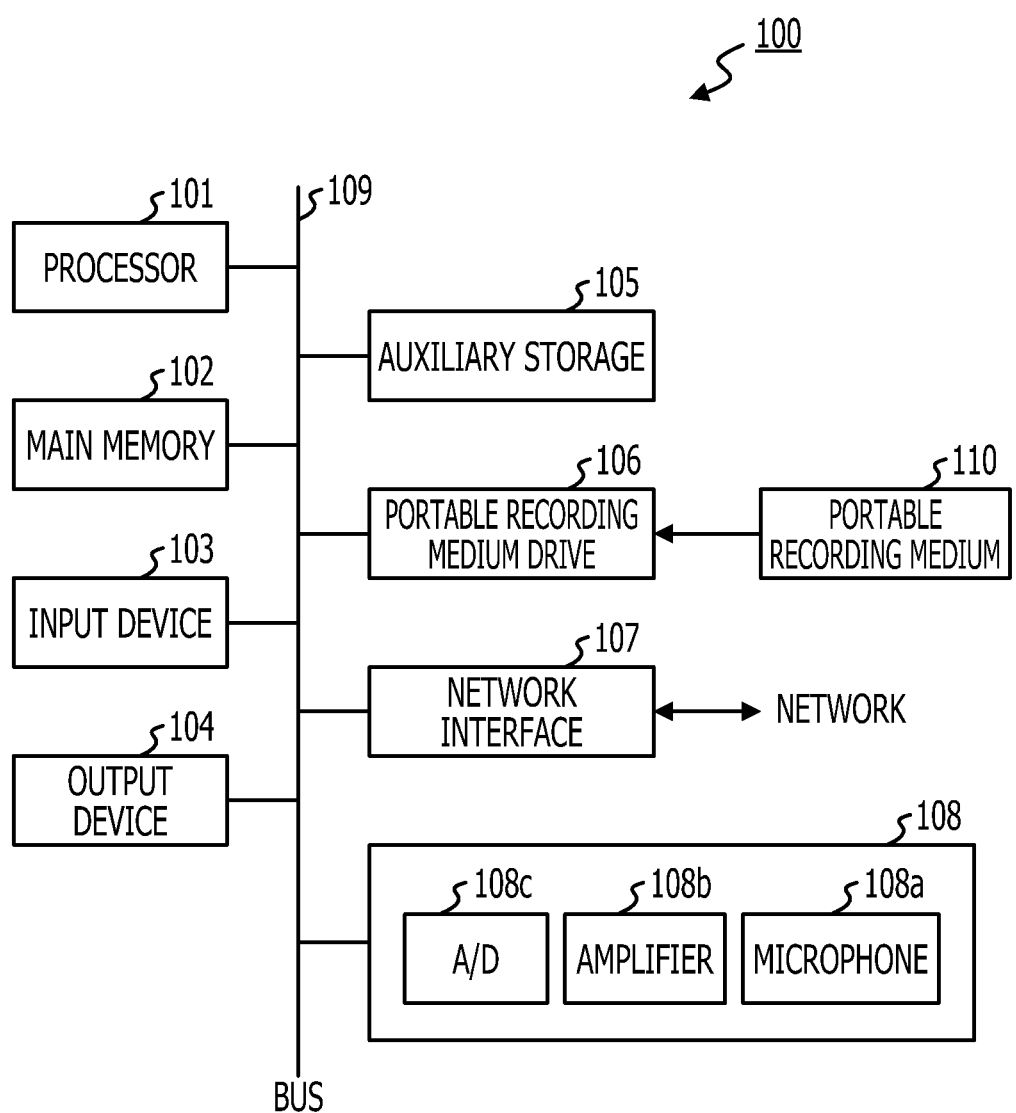
FIG. 2 is a diagram illustrating a hardware configuration example of an apnea episode determination device.

FIG. 2 is a diagram illustrating a hardware configuration example of the apnea episode determination device. The apnea episode determination device may be, for example, an information processing device such as a cell phone handset, a smart phone, a personal digital assistance, a tablet computer, a laptop personal computer, a game console, etc.

An apnea episode determination device 100 includes a processor 101, a main memory 102, an input device 103, an output device 104, an auxiliary storage 105, a portable recording medium drive 106, a network interface 107, and a sound input unit 108. Furthermore, these parts are connected to each other through a bus 109.

The input device 103 may be, for example, operation buttons, a touch panel, a keyboard, a key pad, etc. Data input through the input device 103 is output to the processor 101.

The sound input unit 108 includes a microphone 108a, an amplifier 108b, and an A/D converter 108c. The microphone 108a is arranged near a subject and facing thereto. The microphone 108a collects a breathing sound or any sound which a subject makes and sound signals around the subject. The microphone 108a outputs an electrical signal of collected sound to the amplifier 108b. Hereinafter, the electrical signal corresponding to the sound is referred to as a "sound signal".

The sound signal is amplified by the amplifier 108b and input to the analog-to-digital converter (A/D converter) 108c. The A/D converter 108c converts the sound signal from an analog signal to a digital signal. Sound data converted to the digital signal is output to the processor 101.

The portable recording medium drive 106 reads various types of data or programs recorded in a portable recording medium 110, and outputs to the processor 101. The portable recording medium 110 may be a recoding medium such as, for example, a SD card, a mini SD card, a micro SD card, a universal serial bus (USB) flash memory, a compact disc (CD), a digital versatile disc (DVD), a flash memory card, etc.

The network interface 107 is an interface for inputting and outputting information to and from a network. The network interface 107 connects to a wired network and a wireless network. The network interface 107 may be, for example, a network interface card (NIC), a wireless local area network (LAN) card, etc. Data or the like received by the network interface 107 is output to the processor 101.

The auxiliary storage 105 stores various programs and data to be used by the processor 101 when executing the programs. The auxiliary storage 105 may be a nonvolatile memory such as, for example, an erasable programmable ROM (EPROM), a hard disk drive, etc. The auxiliary storage 105 retains, for example, an operating system (OS), an apnea episode determination program, and other various application programs.

The main memory 102 provides the processor 101 with a work space and a memory space for loading programs stored in the auxiliary storage 105, and also functions as a buffer. The main memory 102 may be a semiconductor memory such as, for example, a random access memory (RAM).

The processor 101 may be, for example, a central processing unit (CPU). The processor 101 performs various processes by executing the OS and various application programs retained in the auxiliary storage 105 or the portable recording medium 110 after loading them into the main memory 102. The number of the processor 101 is not limited to one, and a plurality of the processor 101 may also be included.

The output device 104 outputs results of the processes by the processor 101. The output device 104 includes a sound output device such as loudspeakers or the like, a display, and a printer.

For example, in the apnea episode determination device 100, the processor 101 executes the apnea episode determination program retained in the auxiliary storage 105 after loading the apnea episode determination program into the main memory 102. The apnea episode determination device 100 detects an apnea episode from the sound data of the subject during sleep, which is input through the sound input unit 108, by executing the apnea episode determination program. Note that the foregoing hardware configuration of the apnea episode determination device is provided as one of examples, and the hardware configuration is not limited thereto. Some of constituting elements may be omitted, replaced, or added depending on embodiments. For example, the microphone 108a may be an independent device separated from the apnea episode determination device 100, and may be connected thereto by a cable. Furthermore, hereinafter, the embodiments are described for cases where the apnea episode determination device 100 determines an apnea episode from the sound data of the subject during sleep, which is input through the sound input unit 108. However, the applicable cases are not limited thereto. For example, the apnea episode determination device 100 may determine an apnea episode from sound data which is recorded in advance during sleep of a subject. In such a case, the sound data of the subject during sleep may be, for example, stored in the auxiliary storage 105 or the portable recording medium 110, or input through the network interface 107.

Figure 3:
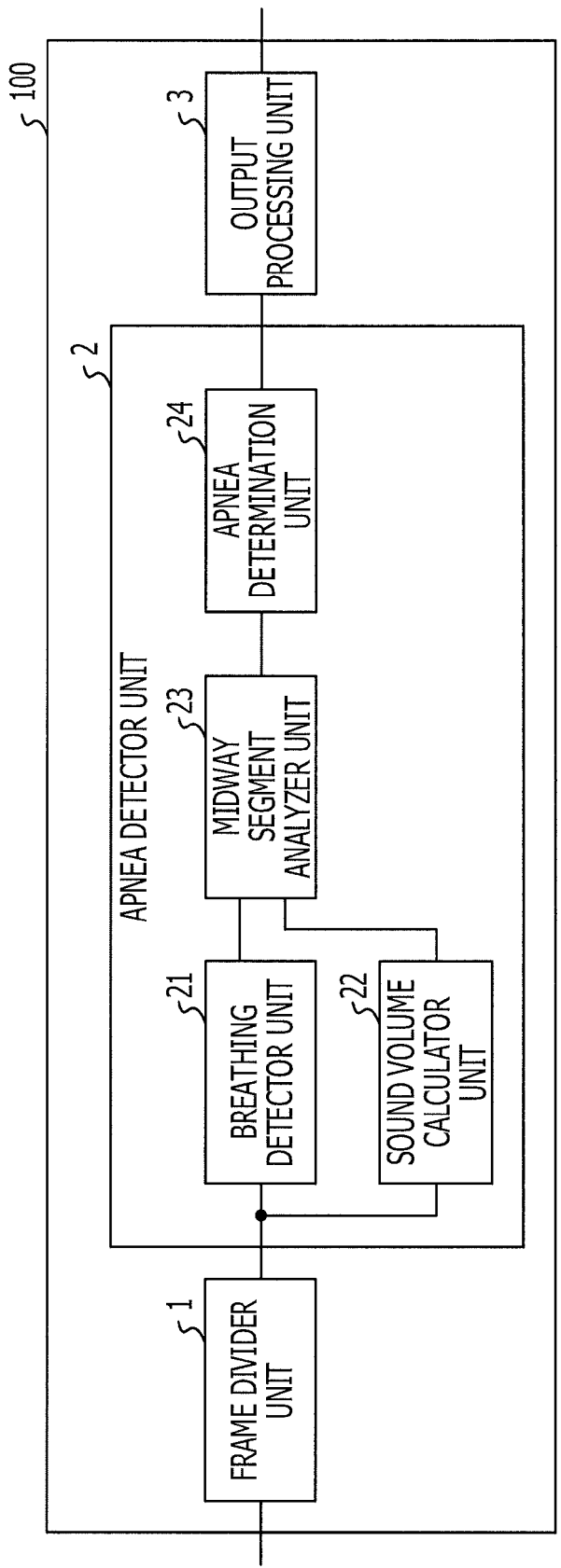
FIG. 3 is a diagram illustrating an example of functional blocks of an apnea episode determination device according to a first embodiment.

FIG. 3 is a diagram illustrating an example of functional blocks of the apnea episode determination device 100 according to the first embodiment. The apnea episode determination device 100 functions as a frame divider unit 1, an apnea detector unit 2, and an output processing unit 3 when the processor 101 executes the apnea episode determination program retained in the auxiliary storage 105. Each functional block of the apnea episode determination device 100 may be realized not only by processing of software by the processor 101, but by hardware. For example, each functional block of the apnea episode determination device 100 may be realized by an electronic circuit such as a large scale integration (LSI), a field-programmable gate array (FPGA), etc.

The frame divider unit 1 divides sound data input through the sound input unit 108 into sound frames, each of which has a preset time length, and outputs the sound frames. Below, in some cases, the sound frame may alternatively be referred to simply as a "frame". For example, the time length of a single frame is 20 ms. The frame divider unit 1 is an example of a "divider unit".

The sound frames output from the frame divider unit 1 are input to the apnea detector unit 2. The apnea detector unit 2 analyzes the sound frames, detects an apnea episode, and outputs an apnea episode detection result. Details of the apnea detector unit 2 will be described below.

The output processing unit 3 performs a preset process on the apnea episode detection result input from the apnea detector unit 2, and outputs the apnea episode detection result to a predetermined device. For example, the output processing unit 3 stores the apnea episode detection result in the auxiliary storage 105, and outputs the apnea episode detection result to the output device 104 when a user's output instruction is input. The apnea episode detection result may be, for example, a detection count of apnea episodes, the respective time lengths of each apnea episode, etc. in the sound data that is input or collected.

(Apnea Detector Unit)

The apnea detector unit 2 includes a breathing detector unit 21, a sound volume calculator unit 22, a midway segment analyzer unit 23, and an apnea determination unit 24.

Sound frames output from the frame divider unit 1 are input to the breathing detector unit 21. The breathing detector unit 21 determines if breathing is present or absent in each frame, and outputs a determination result regarding the presence or absence of breathing in each frame. The method for determining the presence or absence of breathing in each frame to be used in the breathing detector unit 21 is not limited to a certain method. For example, as disclosed in Japanese Laid-open Patent Publication No. 2001-029328, the breathing detector unit 21 may determine the presence or absence of breathing in each frame by comparing a sound volume in each frame with a preset threshold. In such a case, it is determined that breathing is present in a frame when the sound volume is equal to or larger than the preset threshold and that breathing is absent in a frame when the sound volume is less than the preset threshold. Alternatively, for example, a method disclosed in International Publication Pamphlet No. WO 2011/010384 may be employed. Hereinafter, a sound frame that is determined as having breathing by the breathing detector unit 21 will be referred to as a "breathing frame". Furthermore, a sound frame that is determined as having no breathing by the breathing detector unit 21 will be referred to as a "non-breathing frame". The breathing detector unit 21 is an example of a "segment detector unit".

Figure 4:
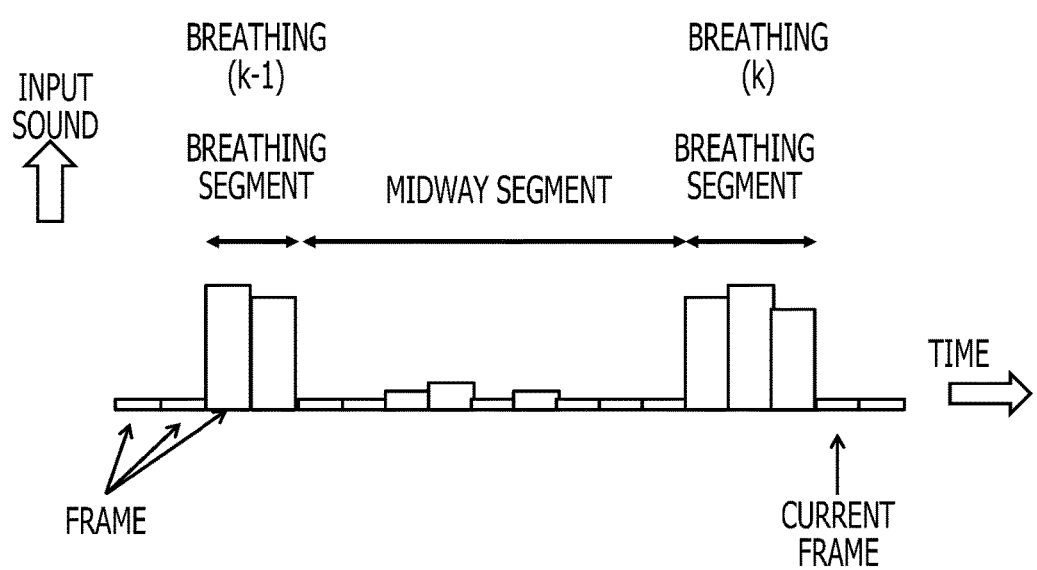
FIG. 4 is a diagram illustrating an example of relationships among sound frames, breathing segments, and a midway segment.

FIG. 4 is a diagram illustrating an example of relations among the sound frames, breathing segments, and the midway segment. In a graph illustrated in FIG. 4, the horizontal axis represents the time and the vertical axis represents the sound volume of input sound. In the apnea episode determination device 100, a segment in which the breathing frames continue is defined as the "breathing segment". Furthermore, a segment in which the non-breathing frames continue is defined as the "midway segment".

Hereinafter, the k-th (k is an integer equal to or larger than zero) breathing segment since the beginning of a detection process of the breathing segment and the midway segment, is denoted as a "breathing(k)". As illustrated in FIG. 4, the midway segment exists between the breathing(k−1) and the breathing(k).

The sound frames output from the frame divider unit 1 are input to the sound volume calculator unit 22. The sound volume calculator unit 22 calculates and outputs the sound volume in each frame. The sound volume S of frame is obtained by the following Equation 1:

$$S(f) = \sum_{t=0}^{M-1} s(t)^2 \qquad \text{(Equation 1)}$$

In Equation 1, f is a frame number (f is an integer equal to or larger than 1) that is assigned to each frame and continuously incremented since the start of sound frame inputs, M is the time length of single frame, and t is the time. Furthermore, s(t) is amplitude (electric power) of an input sound signal.

The midway segment analyzer unit 23 analyzes and outputs the acoustic feature of the midway segment. The acoustic feature may be, for example, the sound volume, an accumulated sound volume, the signal-to-noise ratio, a correlation with a past input sound, etc. The midway segment analyzer unit 23 receives an input of the determination result regarding the presence or absence of breathing in each frame output from the breathing detector unit 21 and an input of the sound volume in each frame output from the sound volume calculator unit 22. The midway segment analyzer unit 23 is an example of a "calculator unit". Details of the midway segment analyzer unit 23 are as follows.

Figure 5:
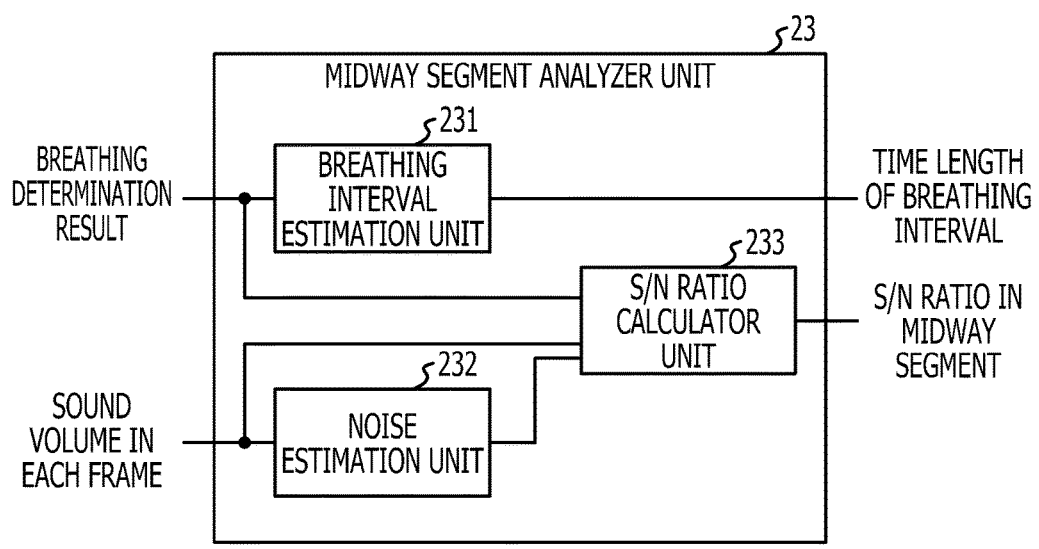
FIG. 5 is a diagram illustrating an example of functional blocks of a midway segment analyzer unit according to the first embodiment.

FIG. 5 is a diagram illustrating an example of functional blocks of a midway segment analyzer unit 23 according to the first embodiment. The midway segment analyzer unit 23 includes a breathing interval estimation unit 231, a noise estimation unit 232, and an S/N ratio calculator unit 233.

The breathing interval estimation unit 231 receives an input of the determination result regarding the presence or absence of breathing in each frame output from the breathing detector unit 21. The breathing interval estimation unit 231 estimates and outputs a length between two breathings (breathing interval), namely, the time length of the midway segment. The breathing interval estimation unit 231 detects the midway segment by detecting borders in the inputs of the determination result regarding the presence or absence of breathing in each frame, the borders being an border at which the breathing frame changes to the non-breathing frame and an border at which the non-breathing frame changes to the breathing frame. The breathing interval estimation unit 231 counts and outputs the number of successive non-breathing frames included in the midway segment as the breathing interval. However, the example is not limited thereto. For example, the breathing interval estimation unit 231 may alternatively calculate the breathing interval (time length of the midway segment) by multiplying the frame length and the number of successive non-breathing frames. The breathing interval estimation unit 231 is an example of a "breathing interval calculator unit".

The sound volume in each frame output from the sound volume calculator unit 22 is input to the noise estimation unit 232. The noise estimation unit 232 estimates and outputs the noise in each frame. The noise estimation unit 232 is an example of an "estimation unit". The noise estimation in each frame may be performed, for example, by using one of the following noise estimation methods 1 and 2.

(Frame Noise Estimation Method 1)

A size (electric power) N(f) of the noise in the frame f is estimated by the following Equation 2:

$$N(f) = \begin{cases} \alpha \cdot N(f-1) + (1-\alpha) \cdot S(f), & (S(f-1) - S(f) < \text{when } \beta) \\ N(f-1), & (\text{otherwise}) \end{cases} \quad \text{(Equation 2)}$$

In Equation 2, $\alpha$ and $\beta$ are fixed values and decided experimentally. Furthermore, an initial value N(0) of the power of noise is decided experimentally.

In Equation 2, the power of noise N(f) of the frame f is updated when a change between the sound volume S(f) of the frame f and the sound volume S(f-1) of the previous frame f-1 is less than the fixed value $\beta$. On the other hand, the power of noise N(f) of the frame f is set equal to the power of noise N(f-1) of the previous frame f-1 when the change between the sound volume S(f) of the frame f and the sound volume S(f-1) of the previous frame f-1 is equal to or larger than the fixed value $\beta$. For example, the fixed value $\alpha$=0.9 and the fixed value $\beta$=2.0.

(Frame Noise Estimation Method 2)

The updating of the noise size may be performed based on a ratio between the sound volume S(f) of the frame f and the power of noise N(f-1) of the previous frame f-1 as expressed in the following Equation 3.

$$N(f) = \begin{cases} \alpha \cdot N(f-1) + (1-\alpha) \cdot S(f), & (S(f) < \text{when } \gamma \cdot N(f-1)) \\ N(f-1), & (\text{otherwise}) \end{cases} \quad \text{(Equation 3)}$$

In Equation 3, $\gamma$ is a fixed value and decided experimentally. Furthermore, an initial value N(0) of the power of noise is decided experimentally.

In Equation 3, the power of noise N(f) of the frame f is updated when the sound volume S(f) of the frame f is less than $\gamma$ (the fixed value) times the power of noise N(f-1) of the previous frame f-1. On the other hand, the power of noise N(f-1) of the previous frame f-1 is set as the power of noise N(f) of the frame f when the sound volume S(f) of the frame f is equal to or larger than $\gamma$ (the fixed value) times the power of noise N(f-1) of the previous frame f-1 or more. For example, the fixed value $\gamma$=2.0.

Note that the methods for estimating the noise in each frame are not limited to the foregoing two examples, and any other method may be applicable.

The S/N ratio calculator unit 233 receives an input of the determination result regarding the presence or absence of breathing in each frame output from the breathing detector unit 21, an input of the sound volume S(f) in each frame output from the sound volume calculator unit 22, and an input of the power of noise N(f) in each frame output from the noise estimation unit 232. The S/N ratio calculator unit 233 calculates and outputs the signal-to-noise ratio in the midway segment based on these inputs.

First, the S/N ratio calculator unit 233 calculates the signal-to-noise ratio in a frame that is determined as the non-breathing frame by the breathing detector unit 21 using the following Equation 4. Hereinafter, when "sig" is used as an index, it denotes the breathing frame. Furthermore, when "no_sig" is used as an index, it denotes the non-breathing frame. No index is used when no distinguishing is made between the breathing frame and the non-breathing frame.

$$SNR_{no\_sig}(f) = \frac{S_{no\_sig}}{N_{no\_sig}} \quad \text{(Equation 4)}$$

Next, the S/N ratio calculator unit 233 calculates the signal-to-noise ratio in the midway segment by using the signal-to-noise ratios thus calculated for the non-breathing frames. For example, the S/N ratio calculator unit 233 calculates a sum, an average value, a weighted average, or the like from the respective signal-to-noise ratios in the non-breathing frames included in the midway segment as the signal-to-noise ratio in the midway segment.

Returning to FIG. 3, the apnea determination unit 24 receives inputs of the breathing interval and the signal-to-noise ratio in the midway segment output from the midway segment analyzer unit 23. The apnea determination unit 24 determines whether or not the midway segment is an apnea episode based on the breathing interval and the signal-to-noise ratio in the midway segment. The apnea determination unit 24 determines that the midway segment is an apnea episode when the following conditions 1 and 2 are satisfied.

(Apnea Episode Determination Conditions)

(Condition 1) Breathing interval threshold 1≤Breathing interval≤Breathing interval threshold 2

(Condition 2) Signal-to-noise ratio in midway segment<Midway segment's signal-to-noise ratio threshold The condition 1 is a condition to confirm that the breathing interval is within a range (10 seconds to 120 seconds), which defines an apnea episode in sleep apnea syndrome. For example, when the breathing interval is the number of the non-breathing frames included in the midway segment and the frame length is 20 ms, the breathing interval threshold 1 is 500 and the breathing interval threshold 2 is 600.

The condition 2 is a condition to confirm that the sound signal included in the midway segment is close to the background noise, namely, that no breathing sound is included in the midway segment. As illustrated in FIG. 1, the signal-to-noise ratio in the segment including the breathing sound becomes larger than the preset threshold while the signal-to-noise ratio in the segment including no breathing sound becomes smaller than the preset threshold. Thus, the midway segment's signal-to-noise ratio threshold is a value of the signal-to-noise ratio with which the midway segment may be considered to have no breathing sound, and the value thereof is set experimentally. When the signal-to-noise ratio in the midway segment is smaller than the midway segment's signal-to-noise ratio threshold, it is more likely that the sound signal included in the midway segment is close to the background noise and no breathing sound is included in the midway segment. The small signal-to-noise ratio in the midway segment represents that an effect of the noise is large in the midway segment.

The apnea determination unit 24 outputs an apnea determination result regarding the midway segment. Subsequently, the apnea determination result regarding the midway segment is output to the predetermined output device 104 by the output processing unit 3 in response to a user's instruction. The apnea determination unit 24 is an example of a "determination unit".

(Operation Example)

Figure 6A:
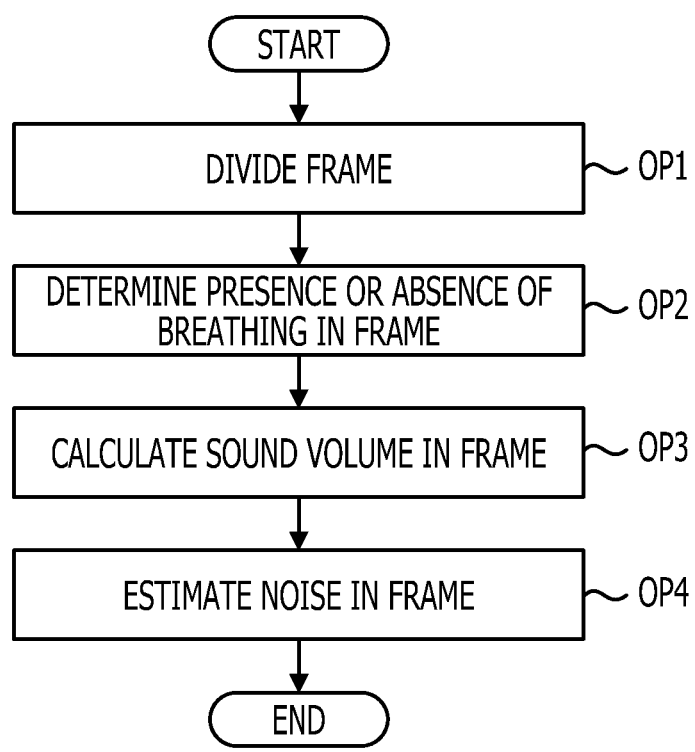
FIG. 6A is an example of a flowchart of processes of an apnea episode determination device.
Figure 6B:
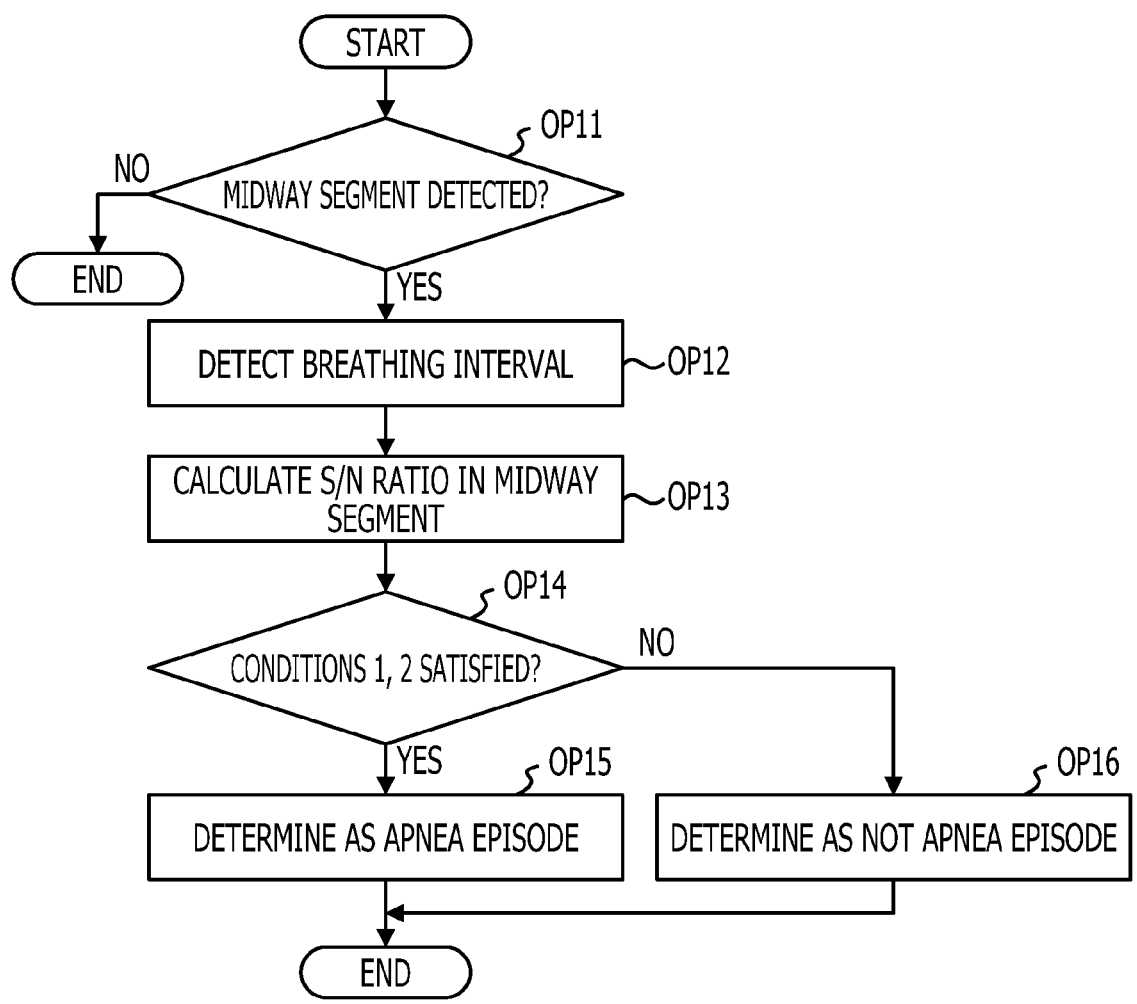
FIG. 6B is an example of a flowchart of processes of an apnea episode determination device.

FIG. 6A and FIG. 6B are examples of flowcharts of the process of the apnea episode determination device 100. The flowcharts of FIG. 6A and FIG. 6B are, for example, performed in parallel. FIG. 6A is the example of the flowchart of the process performed by the apnea episode determination device 100 for each frame. The flowchart illustrated in FIG. 6A may be, for example, repeated by the frame in response to an input of the sound signal (real-time processing) or performed for a sound signal buffered for a preset time period (batch processing). The preset time period is, for example, several minutes to several tens of minutes. Below, both the flowcharts are described for a case where the processor 101 executes the apnea episode determination program stored in the auxiliary storage 105.

In OP1, the processor 101 divides the sound signal into the sound frames, each of which has a preset time length. Next, the process proceeds to OP2. In OP2, the processor 101 determines the presence or absence of breathing in each frame. Next, the process proceeds to OP3. In OP3, the processor 101 calculates the sound volume in each frame. Next, the process proceeds to OP4. In OP4, the processor 101 estimates the noise in each frame. After that, the process illustrated in FIG. 6A ends, and is repeatedly performed from OP1.

The process of OP1 corresponds to the process of the frame divider unit 1. The processes of OP2-OP4 correspond to part of the process of the apnea detector unit 2. More specifically, the process of OP2 corresponds to the process of the breathing detector unit 21. The process of OP3 corresponds to the process of the sound volume calculator unit 22. The process of OP4 corresponds to the process of the noise estimation unit 232. Note that the execution order of the processes of OP2-OP4 is not limited to the above example. The order of these processes may be arbitrarily switched, or the processes may be performed in parallel.

FIG. 6B is the example of the flowchart of the process performed on the midway segment. The flowchart illustrated in FIG. 6B may be, for example, sequentially repeated upon receipt of an execution result of the flowchart of FIG. 6A (real-time processing) or repeated until the process ends for the sound signal buffered for the preset time period (batch processing).

In OP11, the processor 101 determines whether or not the midway segment is detected. The detection of the midway segment is performed, for example, by detecting the borders in successive frames, the borders being a border at which the breathing frame changes to the non-breathing frame and a border at which the non-breathing frame changes to the breathing frame. When the midway segment is not detected (OP11: No), the process illustrated in FIG. 6B ends and the process starts again from OP11.

In OP12, the processor 101 calculates the breathing interval. The breathing interval is obtained, for example, by using the number of the non-breathing frames included in the midway segment. Next, the process proceeds to OP13.

In OP13, the processor 101 calculates the signal-to-noise ratio in the midway segment. The processor 101 calculates the respective signal-to-noise ratios in the non-breathing frames included in the midway segment, and calculates, for example, the sum of these signal-to-noise ratios as the signal-to-noise ratio in the midway segment. Next, the process proceeds to OP14.

In OP14, the processor 101 determines whether or not the condition 1 and the condition 2, which are determining conditions of an apnea episode, are satisfied. That is, the processor 101 determines whether or not the breathing interval meets the definition of apnea episode (Condition 1) and the signal-to-noise ratio in the midway segment is less than the midway segment's signal-to-noise ratio threshold (Condition 2). When the condition 1 and the condition 2 are satisfied (OP14: Yes), the process proceeds to OP15, and the processor 101 determines that the midway segment is an apnea episode (OP15). When at least one of the condition 1 and the condition 2 is not satisfied (OP14: No), the process proceeds to OP16, and the processor 101 determines that the midway segment is not an apnea episode (OP16). Subsequent to the processes of OP15 and OP16, the process illustrated in FIG. 6B ends, and the process starts again from OP11.

The processes of OP11-OP13 correspond to part of the process of the midway segment analyzer unit 23. More specifically, the process of OP11 corresponds to parts of the respective processes performed by the breathing interval estimation unit 231 and the S/N ratio calculator unit 233. The process of OP12 corresponds to part of the process of the breathing interval estimation unit 231. The process of OP13 corresponds to part of the process of the S/N ratio calculator unit 233. Note that the execution order of the processes of OP12 and OP13 is not limited to the above example. The order of these processes may be arbitrarily switched, or the processes may be performed in parallel. The processes of OP14-OP16 correspond to part of the process of the apnea determination unit 24. Note that, when the functional blocks of the apnea episode determination device 100 are realized by their respective hardware components, the processes illustrated in FIG. 6A and FIG. 6B are each performed by the respective hardware components that correspond to the functional blocks.

The apnea episode determination device 100 according to the first embodiment calculates the signal-to-noise ratio in the midway segment, which represents a level of influence of the noise in the midway segment, and determines that the midway segment is an apnea episode when the signal-to-noise ratio in the midway segment is less than the midway segment's signal-to-noise ratio threshold. Thus, an apnea episode may be detected accurately irrespective of the sound volume of the breathing sound and the background noise. Furthermore, in the first embodiment, the power of noise to be used in the calculation of the signal-to-noise ratio is calculated through the noise estimation performed on each frame. Thus, the signal-to-noise ratio becomes a value reflecting a change in background noise characteristics, and the apnea episode determination device 100 according to the first embodiment may detect an apnea episode more accurately even in a case where the background noise fluctuates.

In the second embodiment, the apnea episode determination device analyzes, in addition to the midway segment, the breathing segments before and after the midway segment. More specifically, in the second embodiment, it is analyzed whether or not the breathing sound is included in the breathing segments before and after the midway segment. According to such an arrangement, a more accurate determination may be performed as to whether or not the breathing segment includes the breathing sound, and a more accurate determination may be performed to determine that the midway segment is an apnea episode. In the second embodiment, parts of the description common to the first embodiment will be omitted.

Figure 7:
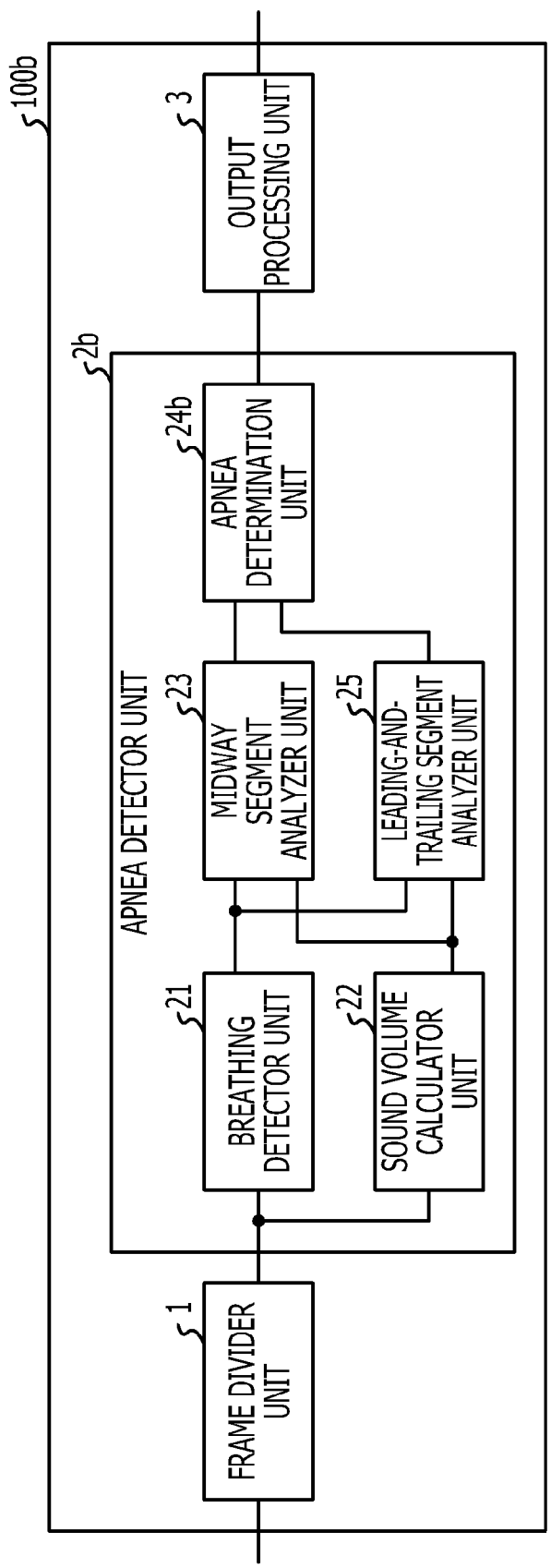
FIG. 7 is an example of a functional block diagram of an apnea episode determination device according to a second embodiment.

FIG. 7 is an example of a functional block diagram of an apnea episode determination device 100b according to the second embodiment. The hardware configuration of the apnea episode determination device 100b according to the second embodiment is similar to that of the apnea episode determination device 100 according to the first embodiment (see FIG. 2).

The apnea episode determination device 100b according to the second embodiment includes a leading-and-trailing segment analyzer unit 25 in an apnea detector unit 2b in addition to the functional blocks of the apnea episode determination device 100 according to the first embodiment. In the second embodiment, processes of a frame divider unit 1, an output processing unit 3, a breathing detector unit 21, a sound volume calculator unit 22, and a midway segment analyzer unit 23 are similar to those in the first embodiment.

The leading-and-trailing segment analyzer unit 25 analyzes the acoustic feature of the breathing segments before and after the midway segment. Hereinafter, the breathing segment immediately before the midway segment in time will be referred to as a "leading breathing segment". Furthermore, the breathing segment immediately after the midway segment in time will be referred to as a "trailing breathing segment". For example, in FIG. 4, the leading breathing segment is the breathing(k−1). The trailing breathing segment is the breathing(k). In some cases, the leading breathing segment and the trailing breathing segment may be collectively referred to as a leading-and-trailing segment. The leading-and-trailing segment analyzer unit 25 is an example of a "second calculator unit".

The leading-and-trailing segment analyzer unit 25 receives an input of the determination result regarding the presence or absence of breathing in each frame from the breathing detector unit 21 and an input of the sound volume in each frame from the sound volume calculator unit 22. Details of the leading-and-trailing segment analyzer unit 25 are as follows.

Figure 8:
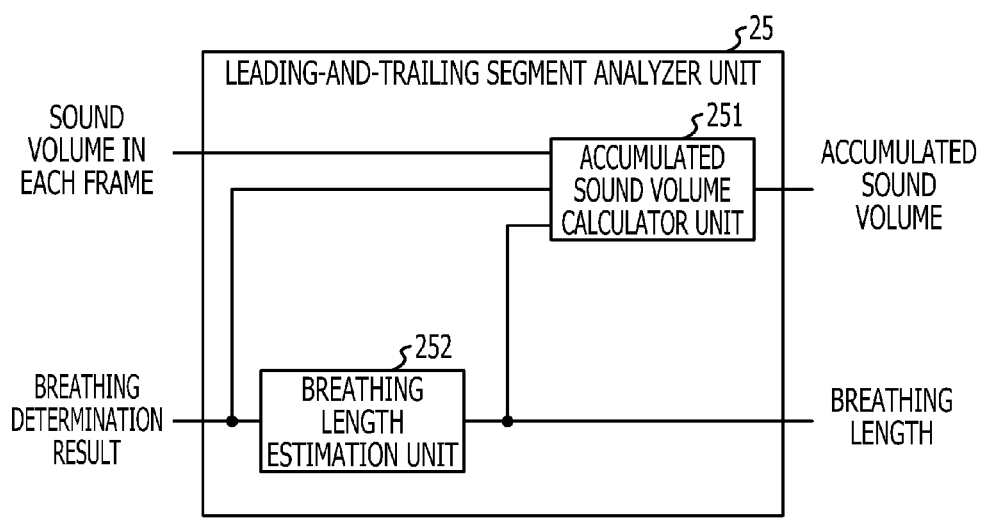
FIG. 8 is a diagram illustrating an example of functional blocks of a leading-and-trailing segment analyzer unit according to the second embodiment.

FIG. 8 is a diagram illustrating an example of functional blocks of the leading-and-trailing segment analyzer unit 25 according to the second embodiment. The leading-and-trailing segment analyzer unit 25 includes an accumulated sound volume calculator unit 251 and a breathing length estimation unit 252.

The breathing length estimation unit 252 receives an input of the determination result regarding the presence or absence of breathing in each frame from the breathing detector unit 21. The breathing length estimation unit 252 counts the number of successive breathing frames and outputs a breathing length "breath_length(k)". That is, the breathing length "breath_length(k)" is the number of the breathing frames included in the breathing segment(k). For example, when three determination results each indicative of the breathing frame are input successively from the breathing detector unit 21, the breathing length "breath_length(k)" of the breathing segment(k) is three.

The accumulated sound volume calculator unit 251 receives an input of the determination result regarding the presence or absence of breathing in each frame output from the breathing detector unit 21, an input of the sound volume in each frame output from the sound volume calculator unit 22, and an input of the breathing length output from the breathing length estimation unit 252. The accumulated sound volume calculator unit 251 calculates and outputs an accumulated sound volume in the breathing segment(k). The accumulated sound volume in the breathing segment(k) is expressed by the following Equation 5:

$$\mathrm{Acc\_}S_{sig}(k) = \sum_{i=0}^{breath\_length(k)-1} S_{sig}(i) \qquad \text{(Equation 5)}$$

where i represents the frame included in the breathing segment(k).

Returning to FIG. 7, in the second embodiment, the apnea determination unit 24b performs the following processes. The apnea determination unit 24b receives inputs of the signal-to-noise ratio in the midway segment and the breathing interval output from the midway segment analyzer unit 23, and inputs of the accumulated sound volume and the breathing length output from the leading-and-trailing segment analyzer unit 25. The apnea determination unit 24b determines whether or not the midway segment is an apnea episode based on those data and outputs an apnea episode detection result. The apnea determination unit 24b determines that the midway segment is an apnea episode when the following conditions 1-6 are satisfied.

(Apnea Episode Determination Conditions)

(Condition 1) Breathing interval threshold 1 ≤ Breathing interval ≤ Breathing interval threshold 2

(Condition 2) Signal-to-noise ratio in midway segment < Midway segment's signal-to-noise ratio threshold (Condition 3) Accumulated sound volume in leading breathing segment>Accumulated sound volume threshold (Condition 4) Breathing length of leading breathing segment>Breathing length threshold (Condition 5) Accumulated sound volume in trailing breathing segment>Accumulated sound volume threshold (Condition 6) Breathing length of trailing breathing segment>Breathing length threshold The condition 1 and the condition 2 are similar to those of the first embodiment. The condition 3 and the condition 5 are conditions to confirm that the sound volume in the breathing segment is large enough to be considered as that of the breathing sound. Thus, the accumulated sound volume threshold is a value with which the breathing segment may be considered to have the breathing sound, and the value is set from statistics of actual sound data. Note that different values may be used for the accumulated sound volume thresholds of the leading breathing segment and the trailing breathing segment.

The condition 4 and the condition 6 are conditions to confirm that the breathing length of the breathing segment is long enough to be considered as that of the breathing sound. Thus, the breathing length threshold is a value with which the breathing segment may be considered to have the breathing sound. For example, the breathing length is a value of 50-500 when the frame length is 20 ms. Note that different values may be used for the breathing length thresholds of the leading breathing segment and the trailing breathing segment.

Accordingly, when the conditions 3-6 are satisfied, the breathing lengths of the breathing segments before and after the midway segment are long enough and the sound volumes thereof are large enough to be considered that these breathing segments include the breathing sound. Thus, it is more likely that each of the breathing segments before and after the midway segment includes the breathing sound. Accordingly, it indicates that the possibility of including no breathing sound in the midway segment is high when that midway segment is positioned in between the breathing segments which are more likely to include the breathing sound. On the other hand, when the conditions 3-6 are not satisfied, it is more likely that no breathing sound is included in the breathing segments before and after the midway segment despite that the breathing detector unit 21 determined as the breathing frames. It is possible that such segments may, for example, include sounds other than the breathing sound (body movement sound or background sound). An apnea episode occurs between breathings. Thus, in a case where the possibility of having no breathing sound in the breathing segments before and after the midway segment is high, the possibility of the midway segment being an apnea episode is low, and thus the midway segment is not determined as an apnea episode.

(Operation Example)

Figure 9:
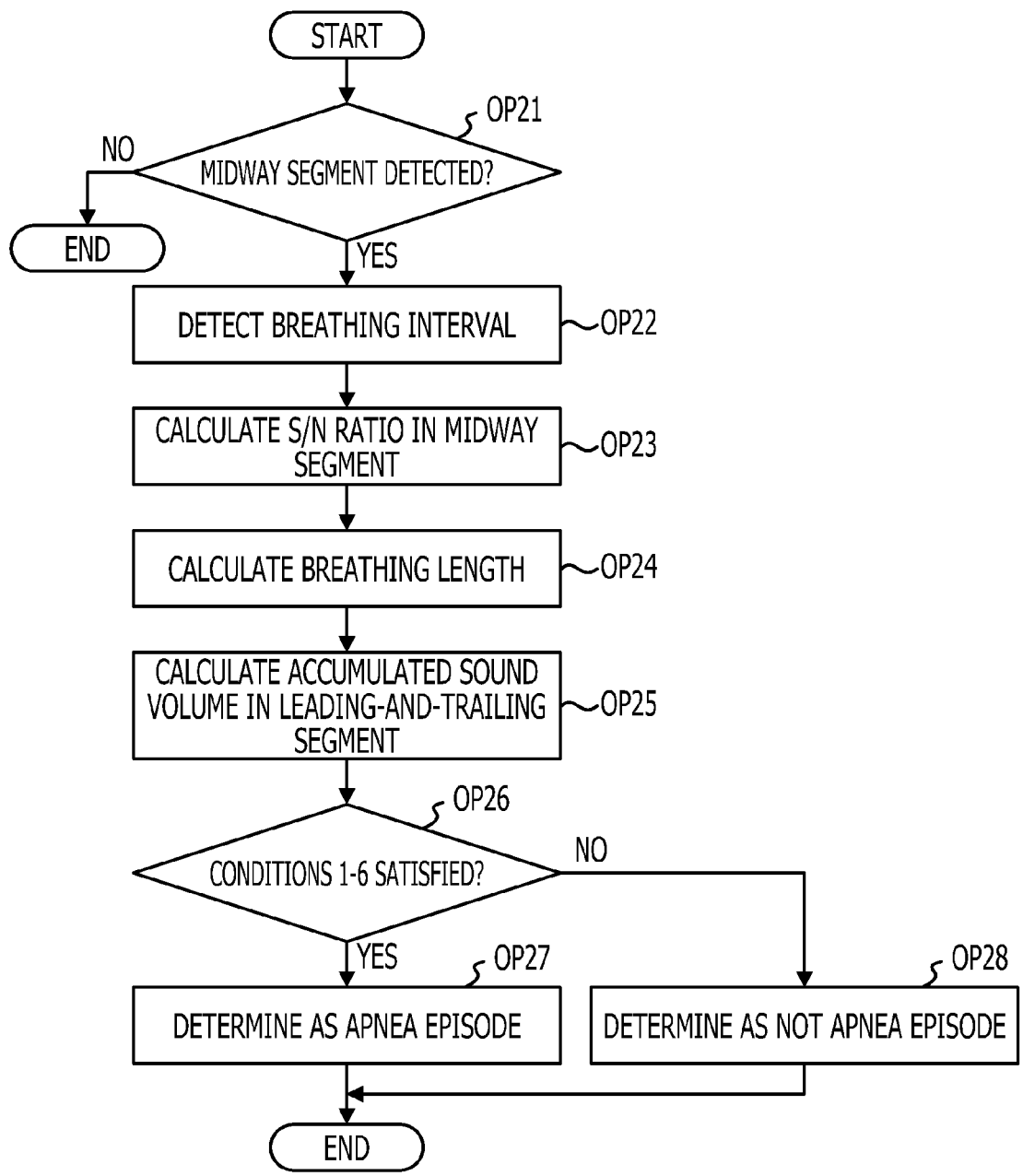
FIG. 9 is an example of a flowchart of processes performed by an apnea episode determination device for each segment.

FIG. 9 is an example of a flowchart of the process performed by the apnea episode determination device 100*b* for each segment. In the second embodiment, the apnea episode determination device 100*b* performed the processes of FIG. 6A for each frame, as is the case with the first embodiment. The flowchart illustrated in FIG. 9 may be, for example, sequentially repeated upon receipt of an execution result of the flowchart of FIG. 6A (real-time processing) or repeated until the process ends for a sound signal buffered for a preset time period (batch processing).

Processes of OP21-OP23 are similar to those of OP11-OP13 of FIG. 6A and calculates the breathing interval and the signal-to-noise ratio in the midway segment when the midway segment is detected. Next, the process proceeds to OP24.

In OP24, the processor 101 calculates the breathing length. The breathing length may be obtained, for example, by counting the number of successive breathing frames. Next, the process proceeds to OP25.

In OP25, the processor 101 calculates the accumulated sound volumes of the leading breathing segment and the trailing breathing segment. Next, the process proceeds to OP26.

In OP26, the processor 101 determines whether or not the conditions 1-6, which are determining conditions of an apnea episode, are satisfied. When the conditions 1-6 are satisfied (OP26: Yes), the process proceeds to OP27, and the processor 101 determines that the midway segment is an apnea episode (OP27). When at least one of the conditions 1-6 is not satisfied (OP26: No), the process proceeds to OP28, and the processor 101 determines that the midway segment is not an apnea episode (OP28). Subsequent to the processes of OP27 and OP28, the process illustrated in FIG. 9 ends, and the process starts again from OP21.

The processes of OP21-OP23 correspond to part of the process of the midway segment analyzer unit 23. The processes of OP24-OP25 correspond to part of the process of the leading-and-trailing segment analyzer unit 25. More specifically, the process of OP24 corresponds to the process of the breathing length estimation unit 252. The process of OP25 corresponds to the process of the accumulated sound volume calculator unit 251. The processes of OP26-OP28 correspond to the process of the apnea determination unit 24*b*. Note that the execution order of the processes of OP22-OP23 and the processes of OP24-OP25 is not limited to the above example. The order of the processes may be arbitrarily switched, or the processes may be performed in parallel. Note that, when the functional blocks of the apnea episode determination device 100*b* are realized by their respective hardware components, the processes illustrated in FIG. 9 are each performed by the respective hardware components that correspond to the functional blocks.

The apnea episode determination device 100*b* according to the second embodiment analyzes not only the midway segment but also the breathing segments before and after the midway segment, and adds a new condition to the apnea determination conditions. The new condition is to confirm that sound signals, which are included in the breathing segments before and after the midway segment, are more likely to be the breathing sound. An apnea episode occurs between breathings. Thus, the apnea episode of the midway segment may be more accurately detected by determining whether or not the breathing sound is included in the breathing segments before and after the midway segment.

In the third embodiment, the apnea episode determination device uses correlations among the midway segment and the breathing segments before and after the midway segment as the acoustic feature based on the background noise component and the signal component excluding the background noise component. More specifically, the apnea episode determination device calculates spectrum distances among the midway segment and the breathing segments before and after the midway segment, and detects that the midway segment is an apnea episode. In the third embodiment, parts of the description common to the first embodiment and the second embodiment will be omitted.

Figure 10A:
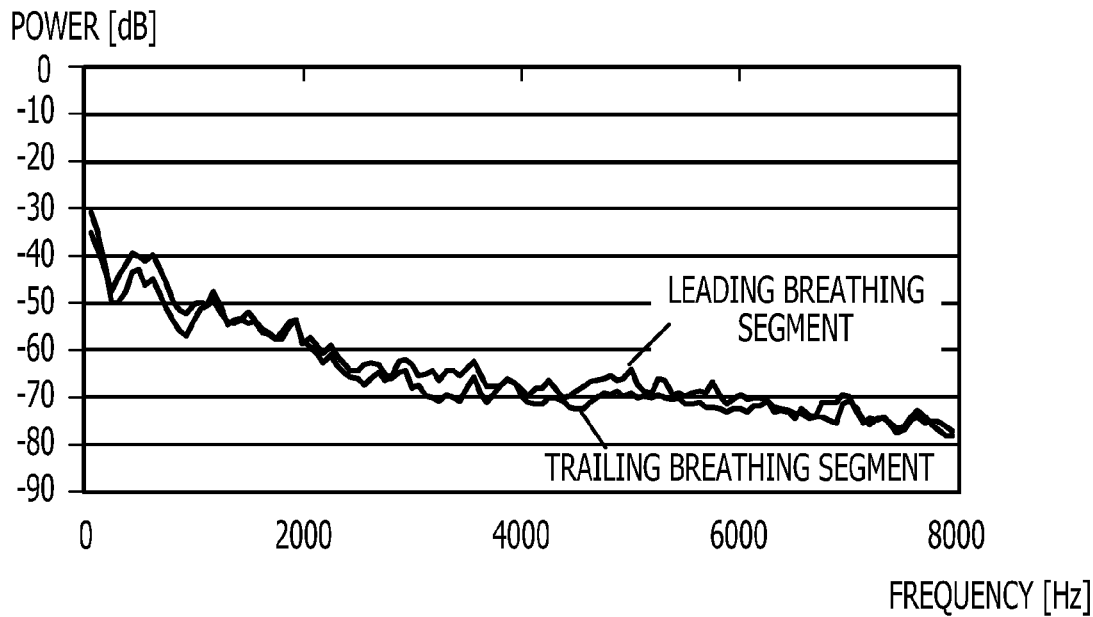
FIG. 10A is a diagram illustrating an example that compares power spectra between a breathing segment immediately before and a breathing segment immediately after a midway segment.

FIG. 10A is a diagram illustrating an example that compares power spectra between the leading breathing segment with the trailing breathing segment relative to one midway segment. FIG. 10A illustrates a power spectrum of the leading breathing segment and a power spectrum of the trailing breathing segment relative to one midway segment included in sound data that is actually measured.

The leading breathing segment and the trailing breathing segment illustrated in FIG. 10A include the breathing sounds from a same person. Frequencies of the breathing sounds from the same person are substantially the same. Thus, as illustrated in FIG. 10A, a distance between the power spectrum of the leading breathing segment and the power spectrum of the trailing breathing segment is close at any given frequency, and the correlation therebetween is high.

Figure 10B:
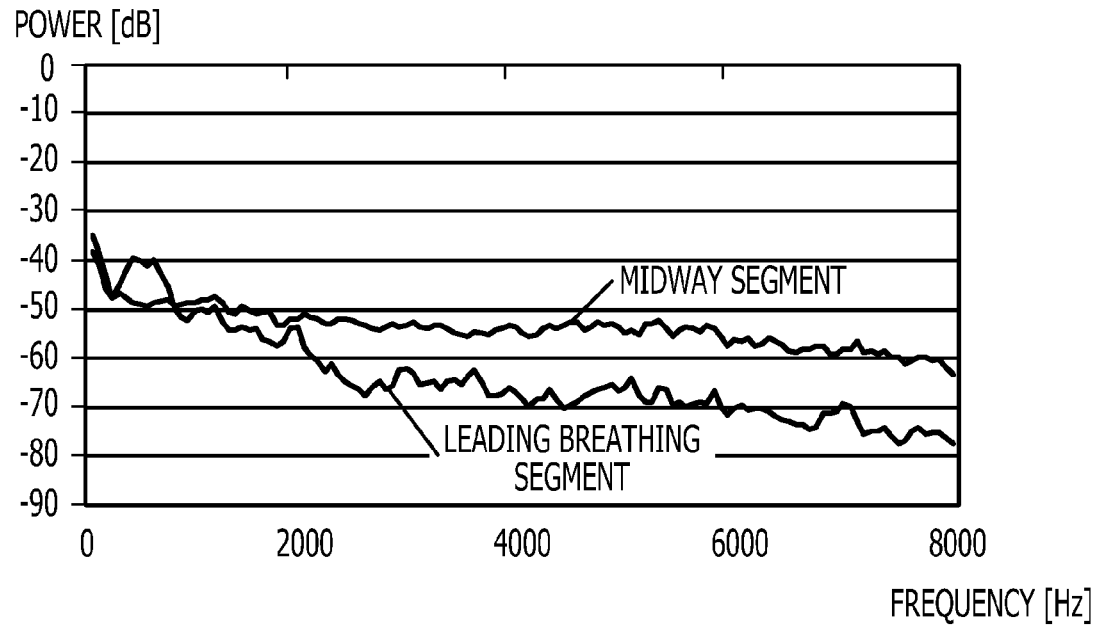
FIG. 10B is a diagram illustrating an example that compares power spectra between a midway segment and a breathing segment immediately before the midway segment.

FIG. 10B is a diagram illustrating an example that compares the power spectrum between the midway segment and the leading breathing segment relative to the midway segment. FIG. 10B illustrates a power spectrum of one midway segment included in sound data that is actually measured, and a power spectrum of the leading breathing segment relative to the midway segment.

In FIG. 10B, the leading breathing segment includes the breathing sound, and the midway segment that is an apnea episode includes no breathing sound. Accordingly, as illustrated in FIG. 10B, the power spectrum of the leading breathing segment and the power spectrum of the midway segment are different in shape, the distances between these spectra are large, and the correlation therebetween is low.

In the third embodiment, the apnea episode determination device determines whether or not the midway segment is an apnea episode by using the distances between the spectra, which changes in response to the correlation level between the midway segment and the breathing segment.

Figure 11:
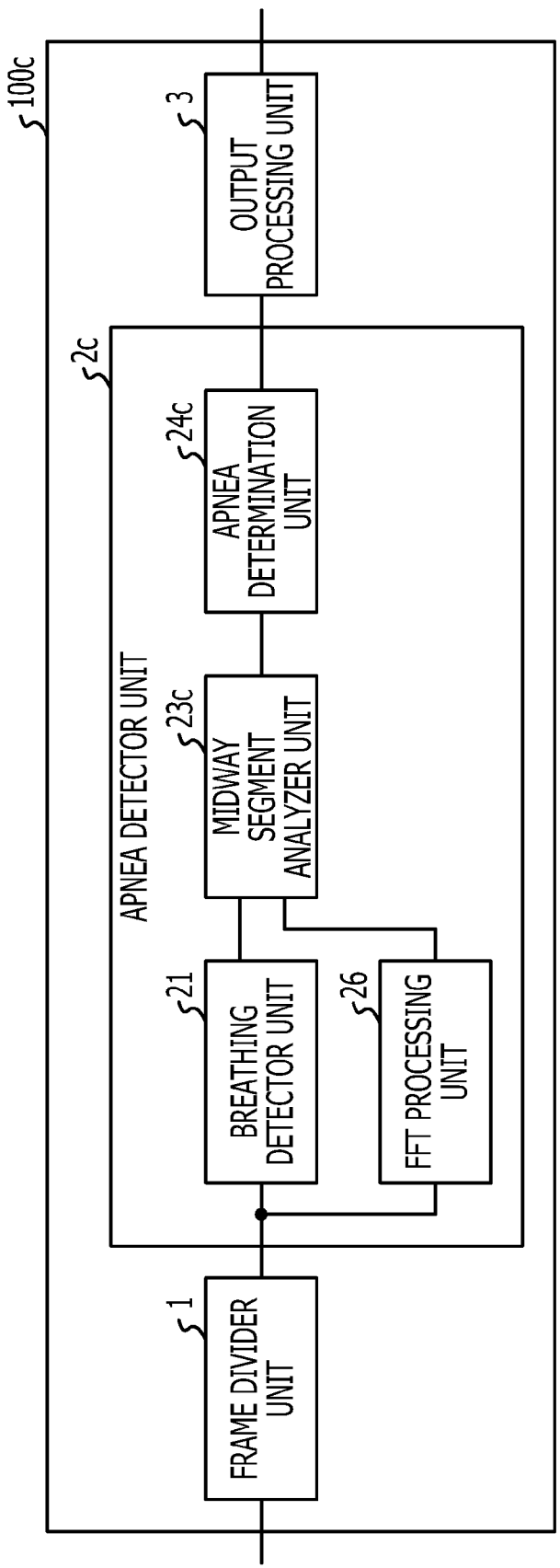
FIG. 11 is an example of a functional block diagram of an apnea episode determination device according to a third embodiment.

FIG. 11 is an example of a functional block diagram of an apnea episode determination device 100c according to the third embodiment. The hardware configuration of the apnea episode determination device 100c according to the third embodiment is similar to that of the apnea episode determination device 100 according to the first embodiment (see FIG. 2).

The apnea episode determination device 100c according to the third embodiment includes a frame divider unit 1, an apnea detector unit 2c, and an output processing unit 3. The apnea detector unit 2c includes a breathing detector unit 21, a midway segment analyzer unit 23c, an apnea determination unit 24c, and a FFT processing unit 26. In the third embodiment, processes of the frame divider unit 1, the output processing unit 3, and the breathing detector unit 21 are similar to those in the first embodiment.

Sound frames output from the frame divider unit 1 are input to the FFT processing unit 26. The FFT processing unit 26 obtains and outputs a FFT signal by performing a Fast Fourier Transform (FFT) processing on a time-domain sound signal for each input frame. The FFT signal "FFT($\omega$)" may be obtained, for example, by the following Equation 6:

$$FFT(\omega)=Re(\omega)+j \cdot Im(\omega), (\omega=0, \ldots, \omega_{max}-1) \quad \text{(Equation 6)}$$

In Equation 6, $\omega$ represents the frequency, $\omega_{max}$ represents the frequency band, and j represents the imaginary number. Note that, although FFT is used in the third embodiment, it is not limited thereto. Other orthogonal transformations such as the Discrete Cosine Transform (DCT), the Modified Discrete Cosine Transform (MDCT), etc. may alternatively be used.

Figure 12:
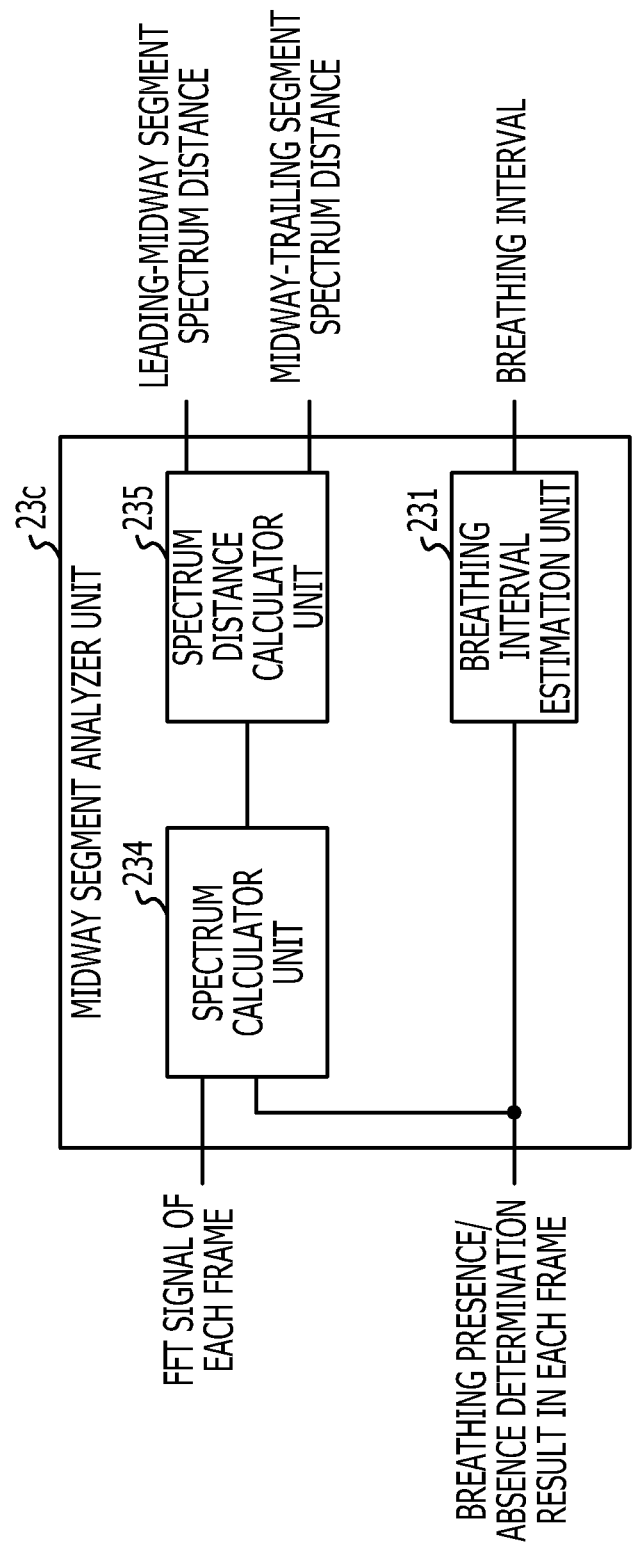
FIG. 12 is a diagram illustrating an example of functional blocks of a midway segment analyzer unit according to the third embodiment.

FIG. 12 is a diagram illustrating an example of functional blocks of the midway segment analyzer unit 23c according to the third embodiment. The midway segment analyzer unit 23c according to the third embodiment includes a breathing interval estimation unit 231, a spectrum calculator unit 234, and a spectrum distance calculator unit 235. A process of the breathing interval estimation unit 231 is similar to that of the first embodiment. The midway segment analyzer unit 23c is an example of the "calculator unit".

The spectrum calculator unit 234 receives an input of the determination result regarding the presence or absence of breathing in each frame from the breathing detector unit 21 and an input of the FFT signal of each frame from the FFT processing unit 26. The spectrum calculator unit 234 calculates a power spectrum for each frame. The power spectrum $P(\omega)$ is obtained as a sum of squares of the real part and the imaginary part of the FFT signal, as the following Equation 7:

$$P(\omega)=Re(\omega)^2+Im(\omega)^2, (\omega=0, \ldots, \omega_{max}-1) \quad \text{(Equation 7)}$$

The spectrum calculator unit 234 calculates respective power spectra of successive breathing frames or successive non-breathing frames, and calculates an average thereof as the power spectrum of one breathing segment or one midway segment. The border between the segments is detected based on a change from the breathing frame to the non-breathing frame or the non-breathing segment to the breathing segment. The spectrum calculator unit 234 outputs the power spectrum of each segment. Note that the power spectrum of each segment is not limited to the average of power spectra of the frames included in each segment, but may also be a weighted average or the like.

The spectrum of each segment output from the spectrum calculator unit 234 is input to the spectrum distance calculator unit 235. The spectrum distance calculator unit 235 calculates spectrum distances between the midway segment and the breathing segments before and after the midway segment. The spectrum distance $D_{pre\_nb}$ between the leading breathing segment and the midway segment is calculated by the following Equation 8:

$$D_{pre\_nb} = \sum_{\omega=0}^{\omega_{max}-1} (P_{pre}(\omega) - P_{nb}(\omega))^2, \quad \text{(Equation 8)}$$

$$(\omega = 0, \ldots, \omega_{max} - 1)$$

$P_{pre}(\omega)$ is the power spectrum of the leading breathing segment. $P_{nb}(\omega)$ is the power spectrum of the midway segment.

The spectrum distance $D_{post\_nb}$ between the midway segment and the trailing breathing segment is calculated by the following Equation 9:

$$D_{post\_nb} = \sum_{\omega=0}^{\omega_{max}-1} (P_{post}(\omega) - P_{nb}(\omega))^2, \quad \text{(Equation 9)}$$

$$(\omega = 0, \ldots, \omega_{max} - 1)$$

$P_{post}(\omega)$ is the power spectrum of the trailing breathing segment.

Returning to FIG. 11, the apnea determination unit 24c receives an input of the spectrum distance between the leading breathing segment and the midway segment, an input of the spectrum distance between the midway segment and the trailing breathing segment, and an input of the breathing interval, output from the midway segment analyzer unit 23c. The apnea determination unit 24c determines whether or not the midway segment is an apnea episode based on the spectrum distance between the leading breathing segment and the midway segment, the spectrum distance between the midway segment and the trailing breathing segment, and the breathing interval. The apnea determination unit 24c determines that the midway segment is an apnea episode when the following conditions A-C are satisfied. Hereinafter, the spectrum distance between the leading breathing segment and the midway segment is referred to as a leading-midway segment spectrum distance. Furthermore, the spectrum distance between the midway segment and the trailing breathing segment is referred to as a midway-trailing segment spectrum distance.

(Apnea Episode Determination Conditions)

(Condition A) Breathing interval threshold 1≤Breathing interval≤Breathing interval threshold 2

(Condition B) Leading-midway segment spectrum distance>Leading-midway segment spectrum distance threshold (Condition C) Midway-trailing segment spectrum distance>Midway-trailing segment spectrum distance threshold The condition A is similar to the condition 1 of the first embodiment, and is a condition to confirm that the breathing interval is within a range (10 seconds to 120 seconds), which defines an apnea episode of sleep apnea syndrome.

The condition B and the condition C are conditions to confirm that the correlations between the midway segment and the breathing segments before and after the midway segment are low. As illustrated in FIG. 10B, the correlation between the breathing segment including the breathing sound and the midway segment including no breathing sound is low, and thus the spectrum distance between these segments is large. The leading-midway segment spectrum distance threshold and the midway-trailing segment spectrum distance threshold may be, for example, values that are determined based on the respective spectrum distances between the breathing segment including breathing sound and the midway segment including no breathing sound, which are included in sound data that is actually measured. Furthermore, the leading-midway segment spectrum distance threshold and the midway-trailing segment spectrum distance threshold may be the same value or different values. When both the leading-midway segment spectrum distance and the midway-trailing segment spectrum distance are larger than their respective thresholds, it indicates that the correlations between the midway segment and the breathing segments before and after the midway segment are low and the possibility of including no breathing sound in the midway segment is high.

Accordingly, the apnea determination unit 24c determines that the midway segment is an apnea episode when the conditions A-C are satisfied, and that the midway segment is not an apnea episode when at least one of the conditions A-C is not satisfied. The apnea determination unit 24c outputs an apnea determination result regarding the midway segment. Subsequently, the apnea determination result regarding the midway segment is output to the predetermined output device 104 by the output processing unit 3 in response to a user's instruction.

(Operation Example)

Figure 13A:
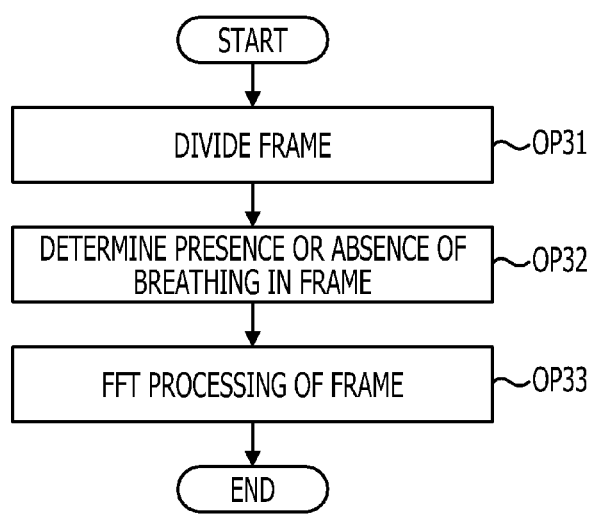
FIG. 13A is an example of a flowchart of processes of an apnea episode determination device.
Figure 13B:
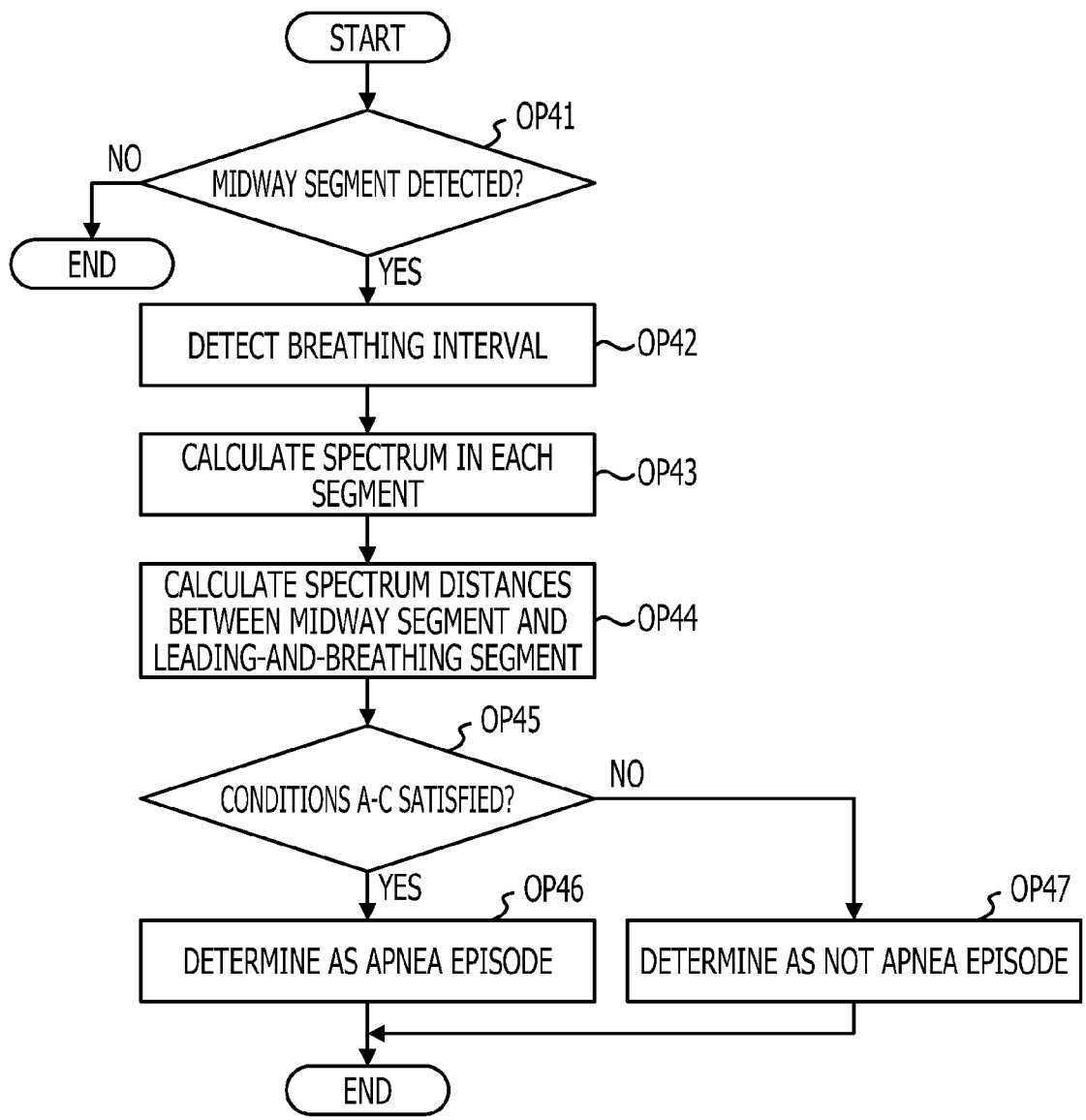
FIG. 13B is an example of a flowchart of processes of an apnea episode determination device.

FIG. 13A and FIG. 13B are examples of flowcharts of the process of the apnea episode determination device 100c. The flowcharts of FIG. 13A and FIG. 13B are performed in parallel. FIG. 13A is the example of the flowchart of the process performed by the apnea episode determination device 100c for each frame. The flowchart illustrated in FIG. 13A may be, for example, repeated by the frame in response to an input of the sound signal (real-time processing) or performed for a sound signal buffered for a preset time period (batch processing). The preset time period is, for example, several minutes to several tens of minutes. Below, the flowcharts are described for a case where the processor 101 executes an apnea episode determination program stored in the auxiliary storage 105.

Processes of OP31 and OP32 are similar to those of OP1 and OP2 of FIG. 6A. That is, the processor 101 divides the sound signal into the sound frames, each of which has a preset time length (OP31), and determines the presence or absence of breathing in each frame (OP32). Next, the process proceeds to OP33. In OP33, the processor 101 performs the Fourier Transformation process for each frame. After that, the process illustrated in FIG. 13A ends, and is repeatedly performed from OP31.

The process of OP31 corresponds to the process of the frame divider unit 1. The processes of OP32-OP33 correspond to part of the process of the apnea detector unit 2c. More specifically, the process of OP32 corresponds to the process of the breathing detector unit 21. The process of OP33 corresponds to the process of the FFT processing unit 26. Note that the execution order of the processes of OP32-OP33 is not limited to the above example. The order of the processes may be arbitrarily switched, or the processes may be performed in parallel.

FIG. 13B is the example of the flowchart of the process performed by the apnea episode determination device 100c for the midway segment and the breathing segment. The flowchart illustrated in FIG. 13B may be, for example, sequentially repeated upon receipt of an execution result of the flowchart of FIG. 13A (real-time processing) or repeated until the process ends for a sound signal buffered for a preset time period (batch processing).

In OP41, the processor 101 determines whether or not the midway segment is detected. The detection of the midway segment is performed, for example, by detecting the borders in successive frames, the borders being a border at which the breathing frame changes to the non-breathing frame and a border at which the non-breathing frame changes to the breathing frame. When the midway segment is detected (OP41: Yes), the process proceeds to OP42. When the midway segment is not detected (OP41: No), the process illustrated in FIG. 13B ends and the process starts again from OP31.

In OP42, the processor 101 calculates the breathing interval. Next, the process proceeds to OP43.

In OP43, the processor 101 calculates the power spectra of the midway segment and the breathing segment. The processor 101 calculates the power spectra of the respective frames included in each segment, and calculates, for example, an average of the power spectra of the respective frames included in each segment as the power spectrum of each segment. Next, the process proceeds to OP44.

In OP44, the processor 101 calculates the leading-midway segment spectrum distance and the midway-trailing segment spectrum distance. Next, the process proceeds to OP45.

In OP45, the processor 101 determines whether or not the conditions A-C, which are determining conditions of an apnea episode, are satisfied. That is, the processor 101 determines whether or not the midway segment's length (the breathing interval) meets the definition of apnea episode (Condition A), and both the leading-midway segment spectrum distance and the midway-trailing segment spectrum distance are larger than their respective thresholds (Conditions B, C). When the conditions A-C are satisfied (OP45: Yes), the process proceeds to OP46, and the processor 101 determines that the midway segment is an apnea episode (OP46). When at least one of the conditions A-C is not satisfied (OP45: No), the process proceeds to OP47, and the processor 101 determines that the midway segment is not an apnea episode (OP47). Subsequent to the processes of OP46 and OP47, the process illustrated in FIG. 13B ends, and the process starts again from OP41.

The processes of OP41-OP44 correspond to part of the process of the midway segment analyzer unit 23c. More specifically, the process of OP41 corresponds to parts of the respective processes performed by the breathing interval estimation unit 231 and the spectrum calculator unit 234. The process of OP42 corresponds to part of the process of the breathing interval estimation unit 231. The process of OP43 corresponds to part of the process of the spectrum calculator unit 234. The process of OP44 corresponds to part of the process of the spectrum distance calculator unit 235. Furthermore, the execution order of the processes of OP42, OP43, and OP44 is not limited to the above example. The order of the processes may be arbitrarily switched, or the processes may be performed in parallel. The processes of OP45-OP47 correspond to part of the process of the apnea determination unit 24c. Note that, when the functional blocks of the apnea episode determination device 100c are realized by their respective hardware components, the processes illustrated in FIG. 13A and FIG. 13B are each performed by the respective hardware components that correspond to the functional blocks.

The apnea episode determination device 100c according to the third embodiment calculates the spectrum distances among the midway segment and the breathing segments before and after the midway segment, and determines that the midway segment is an apnea episode when these spectrum distances are larger than their respective thresholds. When breathing sounds are included in the breathing segments before and after the midway segment, the correlations between the midway segment and breathing segments before and after the midway segment become low, and these spectrum distances become larger than their respective thresholds. Furthermore, even if characteristics of the noise were not fixed, it may still be considered that the correlation between the background noise in the midway segment and the background noise in the breathing segment immediately before or after the midway segment is high. In the third embodiment, the spectrum distance between the midway segment and the breathing segment immediately before or after the midway segment is calculated. Thus, even when the sound signal includes the background noise, the correlations between the midway segment including no breathing sound and the breathing segments including breathing sounds, which are positioned before and after the midway segment, are low. Accordingly, the apnea episode determination device 100c according to the third embodiment may detect an apnea episode more accurately even when the characteristics of the background noise are not fixed. In the third embodiment, the power spectrum is calculated by performing the Fourier transformation for each frame, and the average of the power spectra of the frames included in each segment is calculated as the power spectrum of each segment. However, the example is not limited thereto. For example, the Fourier transformation may be performed once for the frames included in each segment to calculate a power spectrum thereof, and use it as the power spectrum of each segment.

In the fourth embodiment, the apnea episode determination device analyzes, in addition to the midway segment, breathing segments before and after the midway segment. Furthermore, in addition to the spectrum distances between the midway segment and the breathing segments before and after the midway segment, the signal-to-noise ratio in the midway segment is calculated and used as a condition to determine whether or not the midway segment is an apnea episode. According to such an arrangement, a more accurate determination may be performed as to whether or not the breathing segment include the breathing sound, and a more accurate determination may be performed as to whether or not the midway segment is an apnea episode. In the fourth embodiment, parts of the description common to the first to third embodiments will be omitted.

Figure 14:
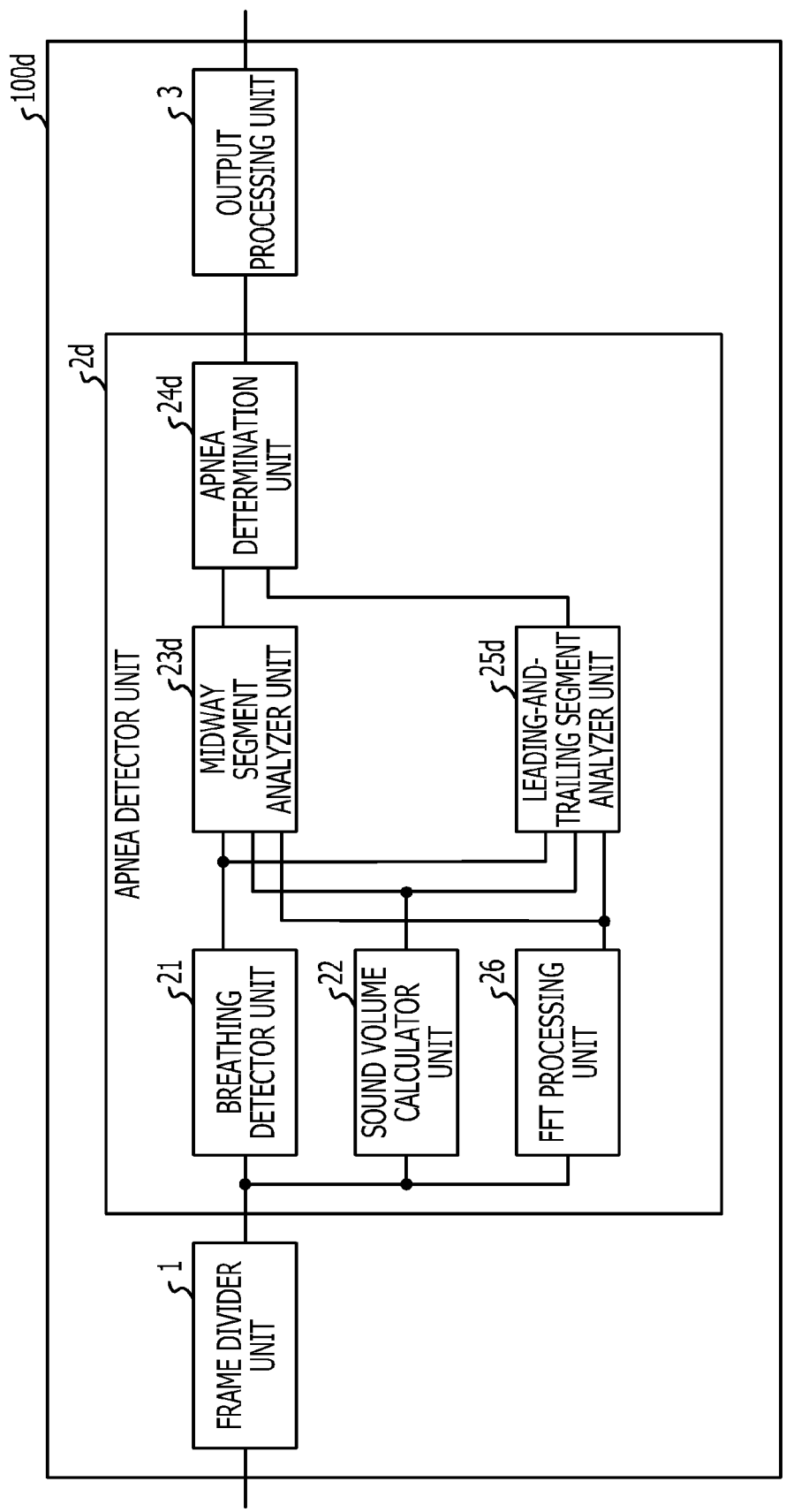
FIG. 14 is an example of a functional block diagram of an apnea episode determination device according to a fourth embodiment.

FIG. 14 is an example of a functional block diagram of an apnea episode determination device 100d according to the fourth embodiment. The hardware configuration of the apnea episode determination device 100d according to the fourth embodiment is similar to that of the apnea episode determination device 100 according to the first embodiment (see FIG. 2).

The apnea episode determination device 100d according to the fourth embodiment includes a sound volume calculator unit 22 and a leading-and-trailing segment analyzer unit 25d in an apnea detector unit 2d in addition to the functional blocks of the apnea episode determination device 100c according to the third embodiment. In the fourth embodiment, processes of a frame divider unit 1, an output processing unit 3, a breathing detector unit 21, and a FFT processing unit 26 are similar to those in the third embodiment. A process of the sound volume calculator unit 22 is similar to that of the first embodiment.

The leading-and-trailing segment analyzer unit 25d receives an input of the determination result regarding the presence or absence of breathing in each frame from the breathing detector unit 21, and an input of the sound volume in each frame from the sound volume calculator unit 22, and an input of the Fourier transformation result of each frame from the FFT processing unit 26. The leading-and-trailing segment analyzer unit 25d is an example of the "second calculator unit". Details of the leading-and-trailing segment analyzer unit 25d is as follows.

Figure 15:
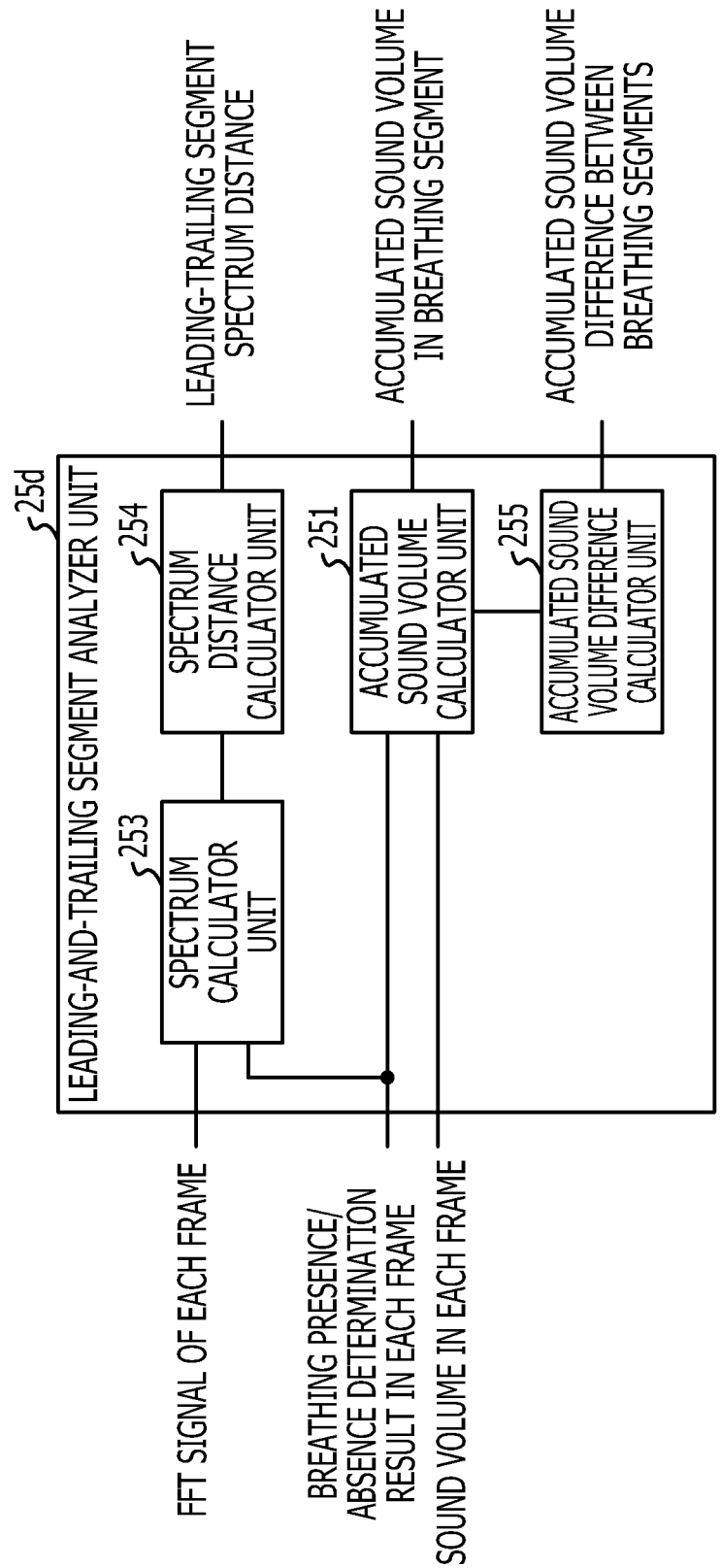
FIG. 15 is a diagram illustrating an example of functional blocks of a leading-and-trailing segment analyzer unit according to the fourth embodiment.

FIG. 15 is a diagram illustrating an example of functional blocks of the leading-and-trailing segment analyzer unit 25d according to the fourth embodiment. The leading-and-trailing segment analyzer unit 25d includes an accumulated sound volume calculator unit 251, a spectrum calculator unit 253, a spectrum distance calculator unit 254, and an accumulated sound volume difference calculator unit 255.

The accumulated sound volume calculator unit 251 performs a process similar to that of the second embodiment. That is, the accumulated sound volume calculator unit 251 accumulates the sound volumes of the breathing frames included in each breathing segment, and outputs the accumulated sound volume in each breathing segment.

The accumulated sound volume in each breathing segment output from the accumulated sound volume calculator unit 251 is input to the accumulated sound volume difference calculator unit 255. The accumulated sound volume difference calculator unit 255 calculates and outputs a difference in the accumulated sound volume between the leading breathing segment and the trailing breathing segment.

The spectrum calculator unit 253 receives an input of the determination result regarding the presence or absence of breathing in each frame output from the breathing detector unit 21 and an input of the Fourier transformed FFT signal of each frame. The spectrum calculator unit 253 calculates the power spectrum of each breathing frame, and calculates an average of the power spectra of the breathing frames included in each segment as the power spectrum of each breathing segment. The power spectrum of each breathing segment may also be, for example, a weighted average of the breathing frames included in the breathing segment. The calculation method of the power spectrum of each breathing segment is similar to that of the spectrum calculator unit 234 according to the third embodiment.

The power spectrum of each breathing segment output from the spectrum calculator unit 253 is input to the spectrum distance calculator unit 254. The spectrum distance calculator unit 254 calculates and outputs a spectrum distance between the leading breathing segment and the trailing breathing segment. The spectrum distance $D_{pre\_post}$ between the leading breathing segment and the trailing breathing segment is calculated by the following Equation 10. Hereinafter, the spectrum distance between the leading breathing segment and the trailing breathing segment is referred to as a leading-trailing segment spectrum distance.

$$D_{pre\_post} = \sum_{\omega=0}^{\omega_{max}-1} (P_{pre}(\omega) - P_{post}(\omega))^2,$$

$$(\omega = 0, \ldots, \omega_{max} - 1)$$

(Equation 10)

Figure 16:
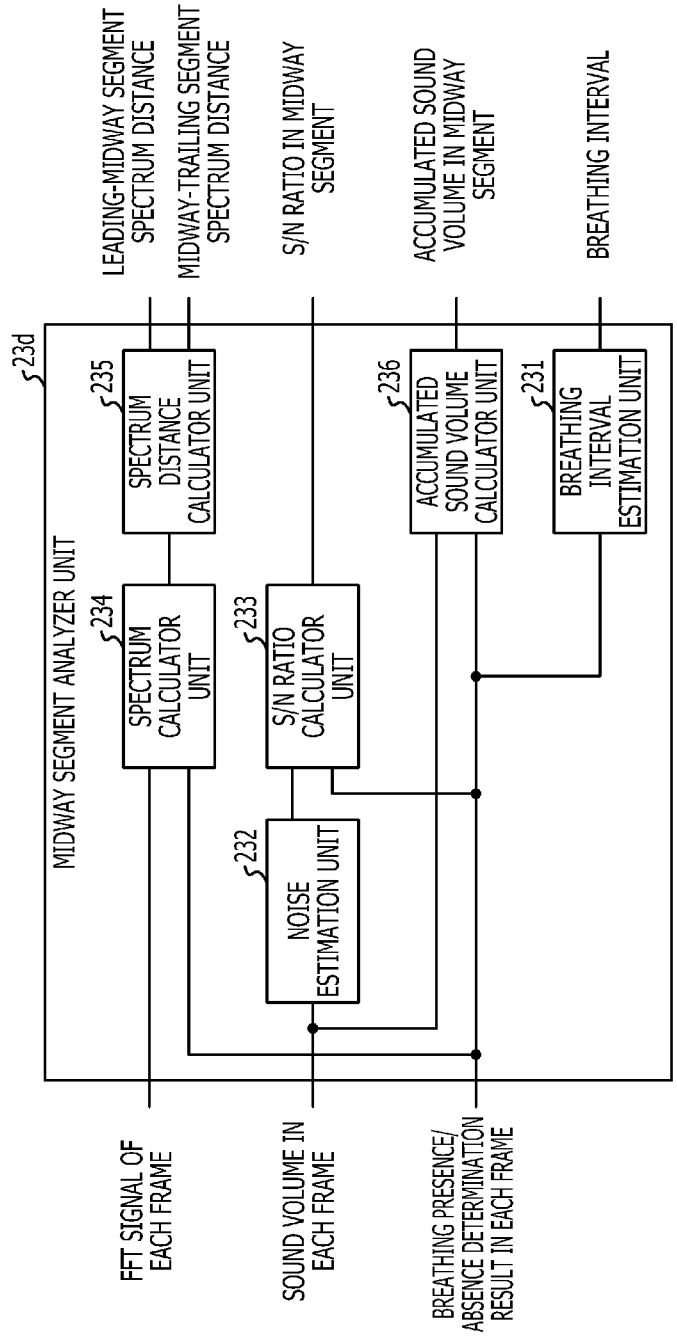
FIG. 16 is a diagram illustrating an example of functional blocks of a midway segment analyzer unit according to the fourth embodiment.

FIG. 16 is a diagram illustrating an example of functional blocks of a midway segment analyzer unit 23d according to the fourth embodiment. The midway segment analyzer unit 23d includes a breathing interval estimation unit 231, a noise estimation unit 232, an S/N ratio calculator unit 233, a spectrum calculator unit 234, a spectrum distance calculator unit 235, and an accumulated sound volume calculator unit 236. The midway segment analyzer unit 23d is an example of the "calculator unit".

The breathing interval estimation unit 231, the noise estimation unit 232, and the S/N ratio calculator unit 233 perform processes similar to those of the first embodiment. The spectrum calculator unit 234 and the spectrum distance calculator unit 235 perform processes similar to those of the third embodiment. That is, the breathing interval estimation unit 231 calculates and outputs the breathing interval. The S/N ratio calculator unit 233 calculates and outputs the signal-to-noise ratio in the midway segment. The spectrum distance calculator unit 235 calculates and outputs the leading-midway segment spectrum distance and the midway-trailing segment spectrum distance.

The accumulated sound volume calculator unit 236 receives an input of the determination result regarding the presence or absence of breathing in each frame output from the breathing detector unit 21 and an input of the sound volume in each frame output from the sound volume calculator unit 22. The accumulated sound volume calculator unit 236 accumulates the sound volumes of the non-breathing frames included in the midway segment, and outputs the accumulated sound volume.

Returning to FIG. 14, in the fourth embodiment, an apnea determination unit 24d performs the following processes. The apnea determination unit 24d receives inputs of the breathing interval, the leading-midway segment spectrum distance, the midway-trailing segment spectrum distance, the signal-to-noise ratio in the midway segment, and the accumulated sound volume in the midway segment output from the midway segment analyzer unit 23d. The apnea determination unit 24d further receives inputs of the accumulated sound volume in each breathing segment, the difference in the accumulated sound volume between the breathing segments before and after the midway segment, and the leading-trailing segment spectrum distance output from the leading-and-trailing segment analyzer unit 25d. The apnea determination unit 24d determines whether or not the midway segment is an apnea episode based on those data and outputs an apnea episode detection result. The apnea determination unit 24d determines that the midway segment is an apnea episode when the following conditions A-I are satisfied.

(Apnea Episode Determination Conditions)

(Condition A) Breathing interval threshold 1≤Breathing interval≤Breathing interval threshold 2

(Condition B) Leading-midway segment spectrum distance>Leading-midway segment spectrum distance threshold (Condition C) Midway-trailing segment spectrum distance>Midway-trailing segment spectrum distance threshold (Condition D) Leading-trailing segment spectrum distance<Leading-trailing segment spectrum distance threshold (Condition E) Signal-to-noise ratio in midway segment<Midway segment's signal-to-noise ratio threshold (Condition F) Accumulated sound volume in midway segment<Midway segment's accumulated sound volume threshold (Condition G) Accumulated sound volume in leading breathing segment>Accumulated sound volume threshold (Condition H) Accumulated sound volume in trailing breathing segment>Accumulated sound volume threshold (Condition I) Accumulated sound volume difference between breathing segments before and after midway segment<threshold for accumulated sound volume difference between breathing segments before and after midway segment The conditions A-C are similar to those of the third embodiment. The conditions E, G, and H are similar to the conditions 2, 3, and 5 of the second embodiment, respectively.

The condition D is a condition to confirm that the breathing segments before and after the midway segment includes breathing sounds. As illustrated in FIG. 10A, when the breathing segments before and after the midway segment include the breathing sounds from a same person, the correlation between the breathing segments before and after the midway segment is high and the spectrum distance therebetween becomes small. When the leading-trailing segment spectrum distance is smaller than the leading-trailing segment spectrum distance threshold, it indicates that the breathing sound is more likely to come from the same person in both breathing segments before and after the midway segment.

The condition F is a condition to confirm that the sound volume in the midway segment is small. When the midway segment includes no breathing sound, the sound volume in the midway segment becomes small. Accordingly, when the sound volume in the midway segment is less than the midway segment's accumulated sound volume threshold, it indicates that the possibility of including no breathing sound in the midway segment is high.

The condition I is a condition to confirm that the sound volumes of the breathing segments before and after the midway segment are close to each other. When the breathing segments before and after the midway segment include the breathing sound, the sound volumes of the breathing segments before and after the midway segment becomes close to each other. Accordingly, when the accumulated sound volume difference between the breathing segments before and after the midway segment is less than the threshold for the accumulated sound volume difference between the breathing segments before and after the midway segment, it indicates that the possibility of including the breathing sound in the breathing segments before and after the midway segment is high.

The leading-trailing segment spectrum distance threshold, the midway segment's accumulated sound volume threshold, the threshold for the accumulated sound volume difference between the breathing segments before and after the midway segment may be set, for example, based on statistics of sound data that is actually measured.

Accordingly, when the conditions A-C and F are satisfied, it indicates that the possibility of including no breathing sound in the midway segment is high. On the other hand, when the conditions A-C and F are not satisfied, the possibility of the midway segment being an apnea episode is low despite that the breathing detector unit 21 determined as the non-breathing frames. It is possible, for example, that a small breathing sound may be included.

Furthermore, when the conditions D, E, and G-I are satisfied, it indicates that the possibility of including the breathing sounds in the breathing segments before and after the midway segment is high. On the other hand, when the conditions D, E, G-I are not satisfied, it is more likely that no breathing sound is included in the breathing segments before and after the midway segment despite that the breathing detector unit 21 determined as the breathing frames. It is possible, for example, that such segments may include sounds other than the breathing sound (body movement sound or background sound). An apnea episode occurs between breathings. Thus, when the possibility of including no breathing sound in the breathing segments before and after the midway segment is high, the possibility of the midway segment being an apnea episode becomes low, and thus the midway segment is not determined as an apnea episode.

(Operation Example)

Figure 17A:
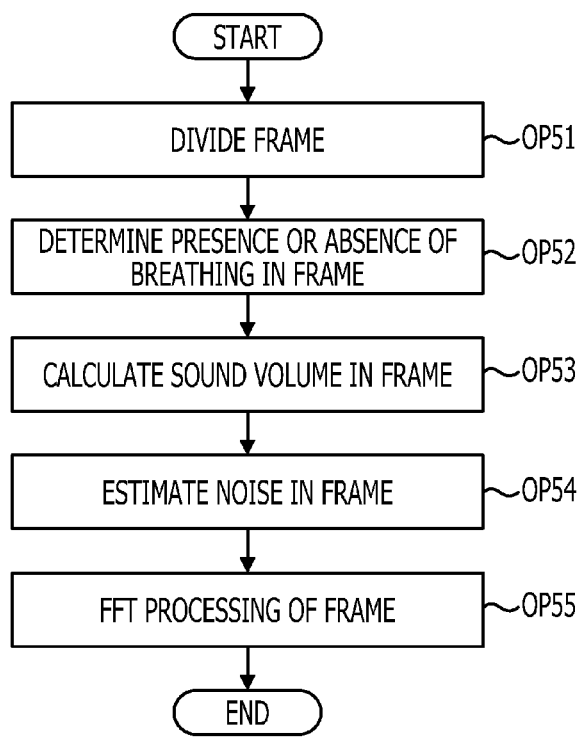
FIG. 17A is an example of a flowchart of processes of an apnea episode determination device.
Figure 17B:
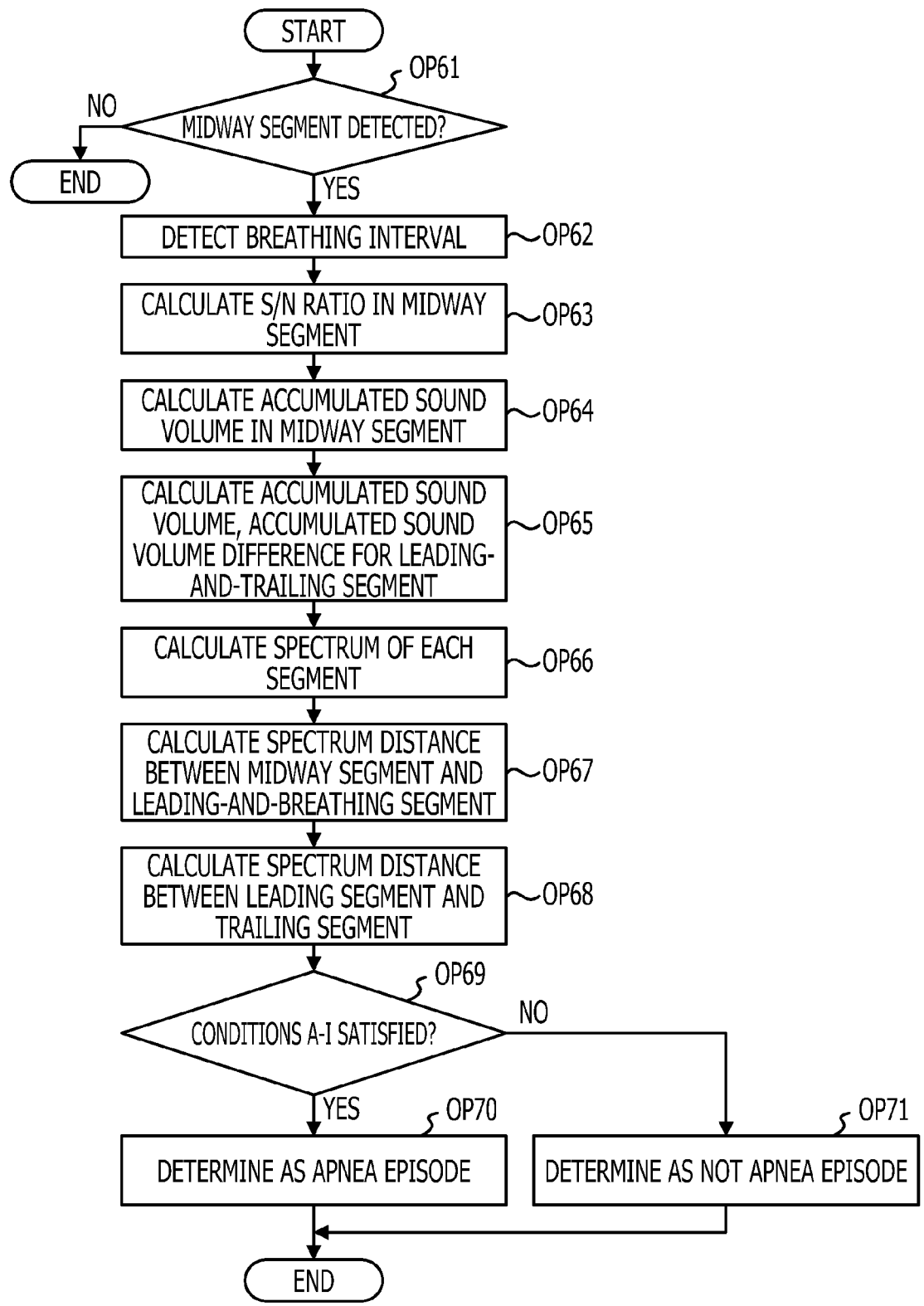
FIG. 17B is an example of a flowchart of processes of an apnea episode determination device.

FIG. 17A and FIG. 17B are examples of flowcharts of the process of the apnea episode determination device 100d. The flowcharts of FIG. 17A and FIG. 17B are performed in parallel. FIG. 17A is the example of the flowchart of the process performed by the apnea episode determination device 100d for each frame. The flowchart illustrated in FIG. 17A may be, for example, repeated by the frame in response to an input of the sound signal (real-time processing) or performed for a sound signal buffered for a preset time period (batch processing). The preset time period is, for example, several minutes to several tens of minutes. Below, the flowcharts are described for a case where the processor 101 executes the apnea episode determination program stored in the auxiliary storage 105.

Processes of OP51-OP54 are similar to the processes of OP1-OP4 of FIG. 6A. Furthermore, a process of OP55 is similar to the process of OP33 of FIG. 13A. That is, the processor 101 divides the sound signal into the sound frames, each of which has a preset time length (OP51), and determines the presence or absence of breathing in each frame (OP52). The processor 101 calculates the sound volume in each frame (OP53), and estimates the noise (OP54). Furthermore, the processor 101 performs the Fourier transformation for each frame (OP55). After that, the process illustrated in FIG. 17A ends, and is repeatedly performed from OP51.

The process of OP51 corresponds to the process of the frame divider unit 1. The processes of OP52-OP55 correspond to part of the process of the apnea detector unit 2d. More specifically, the process of OP52 corresponds to the process of the breathing detector unit 21. The process of OP53 corresponds to part of the process of the sound volume calculator unit 22. The process of OP54 corresponds to part of the process of the noise estimation unit 232. The process of OP55 corresponds to the process of the FFT processing unit 26. Note that the execution order of the process of OP52, a pair of the processes of OP53 and OP54, the process of OP55 is not limited to the above example. The order of the processes may be arbitrarily switched, or the processes may be performed in parallel.

FIG. 17B is the example of the flowchart of the process performed by the apnea episode determination device 100d for the midway segment and the breathing segment. The flowchart illustrated in FIG. 17B may be, for example, sequentially repeated upon receipt of an execution result of the flowchart of FIG. 17A (real-time processing) or repeated until the process ends for a sound signal buffered for a preset time period (batch processing). FIG. 17B is the example of the flowchart of the process performed for each segment.

Processes of OP61-OP63 are similar to those of OP11-OP13 of FIG. 6A and calculates the breathing interval and the signal-to-noise ratio in the midway segment when the midway segment is detected. Next, the process proceeds to OP64.

In OP64, the processor 101 calculates the accumulated sound volume in the midway segment. Next, the process proceeds to OP65.

In OP65, the processor 101 calculates the respective accumulated sound volumes of the leading breathing segment and the trailing breathing segment, and the accumulated sound volume difference between the leading breathing segment and the trailing breathing segment. Next, the process proceeds to OP66.

In OP66, the processor 101 calculates the power spectra of the midway segment and the breathing segment. First, the processor 101 calculates the power spectra of the respective frames included in each segment. Next, the processor 101 calculates, for example, an average of the power spectra of the respective frames as the power spectrum of each segment. Next, the process proceeds to OP67.

In OP67, the processor 101 calculates the leading-midway segment spectrum distance and the midway-trailing segment spectrum distance. Next, the process proceeds to OP68.

In OP68, the processor 101 calculates the leading-trailing segment spectrum distance. Next, the process proceeds to OP69.

In OP69, the processor 101 determines whether or not the conditions A-I, which are determining conditions of an apnea episode, are satisfied. When the condition A to the condition I are satisfied (OP69: Yes), the process proceeds to OP70, and the processor 101 determines that the midway segment is an apnea episode (OP70). When at least one of the condition A to the condition I is not satisfied (OP69: No), the process proceeds to OP71, and the processor 101 determines that the midway segment is not an apnea episode (OP71). Subsequent to the processes of OP70 and OP71, the process illustrated in FIG. 17B ends, and the process starts again from OP61.

The processes of OP61-OP64, OP66, and OP67 correspond to part of the process of the midway segment analyzer unit 23d. The processes of OP65, OP66, and OP68 correspond to part of the process of the leading-and-trailing segment analyzer unit 25d. More specifically, the process of OP62 corresponds to part of the process of the breathing interval estimation unit 231. The process of OP63 corresponds to part of the process of the S/N ratio calculator unit 233. The process of OP64 corresponds to part of the process of the accumulated sound volume calculator unit 236. The process of OP65 corresponds to parts of the processes of the accumulated sound volume calculator unit 251 and the accumulated sound volume difference calculator unit 255. The process of OP66 corresponds to parts of the processes of the spectrum calculator unit 234 and the spectrum calculator unit 253. The process of OP67 corresponds to part of the process of the spectrum distance calculator unit 235. The process of OP68 corresponds to part of the process of the spectrum distance calculator unit 254. The processes of OP69-OP71 correspond to the process of the apnea determination unit 24*d*. Note that, when the functional blocks of the apnea episode determination device 100*d* are realized by their respective hardware components, the processes illustrated in FIG. 17A and FIG. 17B are each performed by the respective hardware components that correspond to the functional blocks.

The apnea episode determination device 100*d* according to the fourth embodiment analyzes not only the midway segment but also the breathing segments before and after the midway segment, and adds a new condition to the apnea determination conditions. The new condition is to confirm that sound signals, which are included in the breathing segments before and after the midway segment, are more likely to be the breathing sound. An apnea episode occurs between breathings. Thus, the apnea episode of the midway segment may be more accurately detected by determining whether or not the breathing sound is included in the breathing segments before and after the midway segment. Furthermore, in the fourth embodiment, the determination as to whether the midway segment is an apnea episode is performed by using the signal-to-noise ratio in the midway segment in addition to the spectrum distances between the midway segment and the breathing segments before and after the midway segment. According to such an arrangement, an apnea episode may be detected more accurately even when characteristics of the background noise changes.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An apnea episode determination device comprising:
a processor; and
a memory which stores a plurality of instructions, which when executed by the processor, cause the processor to execute,
dividing a sound signal from a subject during sleep into a plurality of frames, respective frames among the plurality of frames having a preset time length;
determining whether the respective frames include a breathing sound of the subject;
detecting, based on the determining, a breathing segment and a midway segment from the respective frames, the breathing segment having respective frames including the breathing sound, the midway segment having respective frames excluding the breathing sound and the midway segment existing between the breathing segments;
calculating a time length of the midway segment by counting a number of successive respective frames excluding the breathing sound in the midway segment;
calculating an acoustic feature based on a background noise component and a signal component excluding the background noise component, which are included in the midway segment; and
determining the midway segment is an apnea episode based on the time length of the midway segment and the acoustic feature, even when the background noise component fluctuates, when the acoustic feature meets a first preset condition and the time length of the midway segment is within a preset range,
wherein the acoustic feature is a signal-to-noise ratio in the midway segment calculated from one of a calculated sum, an average value and a weighted average of respective signal-to-noise ratios in the respective frames excluding the breathing sound included in the midway segment, and the first preset condition is when the signal-to-noise ratio is less than a preset threshold,
thereby the apnea episode is detected more accurately regardless of the background noise.

2. The device according to claim 1, further comprising:
the memory which stores a plurality of instructions, which when executed by the processor, cause the processor to further execute,
estimating a power of noise included in the sound signal in the respective frames among the plurality of frames having the preset time length,
wherein the signal-to-noise ratio in the midway segment is calculated based on the power of noise.

3. The device according to claim 2,
wherein the power of noise in one frame is estimated based on the power of noise in a last frame before the one frame and a sound volume of the sound signal included in the one frame when an amount of change in the volume of the sound signal included in the one frame is less than a preset value.

4. The device according to claim 2,
wherein the power of noise in one frame is estimated based on the power of noise in a last frame before the one frame and a sound volume of the sound signal included in the one frame when a ratio is less than a preset ratio, the ratio being a relationship between the volume of the sound signal included in the one frame and the power of noise of the last frame before the one frame.

5. The device according to claim 1, further comprising:
calculating an acoustic feature of at least one of the sound signals of the breathing segments immediately before and immediately after the midway segment,
wherein the midway segment is further determined as an apnea episode when the acoustic feature of the sound signal in the midway segment and the acoustic feature of at least one of the sound signals in the breathing segments immediately before and immediately after the midway segment meet preset conditions.

6. The device according to claim 5,
wherein a time length of at least one of the sound signals in the breathing segments is calculated immediately before and immediately after the midway segment, and the midway segment is further determined as an apnea episode when the acoustic feature of the sound signal in the midway segment meets the first preset condition and the time length of the midway segment is longer than a preset threshold.

7. The device according to claim 5,
wherein the processor executes calculating an accumulated sound volume of at least one of the sound signals in the breathing segments immediately before and immediately after the midway segment, and the midway segment is further determined as an apnea episode when the acoustic feature of the sound signal in the midway segment meets the first preset condition and the accumulated sound volume is larger than a preset threshold.

8. The device according to claim 5,
wherein the processor executes calculating a difference in accumulated sound volume between the sound signals in the breathing segments immediately before and immediately after the midway segment, and the midway segment is further determined as an apnea episode when the acoustic feature of the sound signal in the midway segment meets the first preset condition and the difference in accumulated sound volume is less than a preset threshold.

9. The device according to claim 5,
wherein the processor executes calculating a spectrum distance between the sound signals in the breathing segments immediately before and immediately after the midway segment, and the midway segment is further determined as an apnea episode when the acoustic feature of the sound signal in the midway segment meets the first preset condition and the spectrum distance is less than a preset threshold.

10. The device according to claim 1,
wherein the calculating the time length of the midway segment is calculated by multiplying the number of successive respective frames excluding the breathing sound in the midway segment and the preset time length of the respective frames excluding the breathing sound in the midway segment.

11. An apnea episode determination method comprising:
dividing a sound signal from a subject during sleep into a plurality of frames, respective frames among the plurality of frames having a preset time length;
determining whether the respective frames include a breathing sound of the subject;
detecting, based on the determining, a breathing segment and a midway segment from the respective frames, the breathing segment having respective frames including the breathing sound, the midway segment having respective frames excluding the breathing sound and the midway segment existing between the breathing segments;
calculating a time length of the midway segment by counting a number of successive respective frames excluding the breathing sound in the midway segment;
calculating, by a computer processor, an acoustic feature based on a background noise component and a signal component excluding the background noise component, which are included in the midway segment; and
determining the midway segment is an apnea episode based on the time length of the midway segment and the acoustic feature, even when the background noise component fluctuates, when the acoustic feature meets a first preset condition and the time length of the midway segment is within a preset range, wherein the acoustic feature is a signal-to-noise ratio in the midway segment, calculated from one of a calculated sum, an average value and a weighted average of respective signal-to-noise ratios in the respective frames excluding the breathing sound included in the midway segment and the first preset condition is when the signal-to-noise ratio is less than a preset threshold,
thereby the apnea episode is detected more accurately regardless of the background noise.

12. An apnea episode determination device comprising:
a processor; and
a memory which stores a plurality of instructions, which when executed by the processor, cause the processor to execute,
dividing a sound signal from a subject during sleep into a plurality of frames, respective frames among the plurality of frames having a preset time length;
determining whether the respective frames include a breathing sound of the subject;
detecting, based on the determining, a breathing segment and a midway segment from the respective frames, the breathing segment having respective frames including the breathing sound, the midway segment having respective frames excluding the breathing sound and the midway segment existing between the breathing segments;
calculating a time length of the midway segment by counting a number of successive respective frames excluding the breathing sound in the midway segment;
calculating an acoustic feature based on a background noise component and a signal component excluding the background noise component, which are included in the midway segment; and
determining the midway segment is an apnea episode based on the time length of the midway segment, the acoustic feature and a correlation between the sound signal in the midway segment and at least one of the sound signals in the breathing segments immediately before and immediately after the midway segment, even when the background noise component fluctuates, when the acoustic feature meets a first preset condition and the time length of the midway segment is within a preset range,
wherein the first preset condition is when the correlation is less than a preset threshold,
wherein the acoustic feature is a signal-to-noise ratio in the midway segment calculated from one of a calculated sum, an average value and a weighted average of respective signal-to-noise ratios in the respective frames excluding the breathing sound included in the midway segment, and the first preset condition is when the signal-to-noise ratio is less than a preset threshold,
thereby the apnea episode is detected more accurately regardless of the background noise.

13. The apnea episode determination device according to claim 12, wherein the correlation is calculated based on a difference in power spectrum between the sound signal in the midway segment and at least one of the sound signals in the breathing segments immediately before and immediately after the midway segment.

* * * * *